United States Patent
Mou et al.

(10) Patent No.: US 11,278,242 B2
(45) Date of Patent: Mar. 22, 2022

(54) WEARABLE HEALTH MONITORING DEVICE

(71) Applicant: Microjet Technology Co., Ltd., Hsinchu (TW)

(72) Inventors: Hao-Jan Mou, Hsinchu (TW); Ching-Sung Lin, Hsinchu (TW); Chi-Feng Huang, Hsinchu (TW); Yung-Lung Han, Hsinchu (TW); Chun-Yi Kuo, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 235 days.

(21) Appl. No.: 16/656,248

(22) Filed: Oct. 17, 2019

(65) Prior Publication Data

US 2020/0129122 A1    Apr. 30, 2020

(30) Foreign Application Priority Data

Oct. 31, 2018    (TW) .................................. 107138685

(51) Int. Cl.
*A61B 5/00* (2006.01)
*A61B 5/024* (2006.01)

(52) U.S. Cl.
CPC ............ *A61B 5/681* (2013.01); *A61B 5/0022* (2013.01); *A61B 5/02438* (2013.01); *A61B 5/746* (2013.01); *A61B 2562/0247* (2013.01)

(58) Field of Classification Search
CPC . A61B 5/681; A61B 5/02438; A61B 5/02141; A61B 5/02225; A61B 5/02233;

(Continued)

(56) References Cited

U.S. PATENT DOCUMENTS 6,475,153 B1*  11/2002  Khair .................... G08B 25/08
                                                      600/485
2008/0177187 A1*  7/2008  Lee .................... A61B 5/02233
                                                      600/490

(Continued)

FOREIGN PATENT DOCUMENTS

CN    102613966 A    8/2012
CN    205197978 U    5/2016

(Continued)

*Primary Examiner* — Sean P Dougherty
*Assistant Examiner* — Jonathan E. Cooper
(74) *Attorney, Agent, or Firm* — Birch, Stewart, Kolasch & Birch, LLP

(57) ABSTRACT

A wearable health monitoring includes a monitoring main-body, a wearable component and a biometric monitoring module. The wearable component is connected with the monitoring main-body. The biometric monitoring module is disposed within the monitoring main-body and includes a photoelectric sensor, a pressure sensor and an air-pressure-based blood pressure meter. The air-pressure-based blood pressure meter is embedded and positioned in the embedding slot portion of the embedding seat, and includes a gas-collecting actuator and an elastic air-bag. The gas-collecting actuator transports a gas to the elastic air-bag, and the elastic air-bag is inflated and elastically protrudes to attach to a skin tissue of a wearing user. The pressure sensor measures vasoconstriction pulsation under the skin tissue. A detection signal is generated and converted into health data information, which is outputted to the photoelectric sensor for calibrating a calculation of detection thereof to output precise health data information.

20 Claims, 20 Drawing Sheets

(58) Field of Classification Search
CPC ............ A61B 5/02416; A61B 5/02154; A61B 5/0295; A61B 5/6824; A61B 5/0022; A61B 5/746; A61B 2562/0247; A61B 2562/16; A61B 5/02255; A61B 5/02133
See application file for complete search history.

(56) References Cited

U.S. PATENT DOCUMENTS

| | | | |
|---|---|---|---|
| 2012/0059237 A1* | 3/2012 | Amir .................... | A61B 5/0285 600/365 |
| 2016/0287103 A1* | 10/2016 | Saponas ............. | A61B 5/02444 |
| 2017/0222125 A1* | 8/2017 | Chen .................... | F16K 99/0048 |
| 2017/0241834 A1* | 8/2017 | Lin ....................... | G01J 1/0407 |
| 2019/0125201 A1* | 5/2019 | Lee ..................... | A61B 5/02125 |
| 2020/0178812 A1* | 6/2020 | Zhang ................... | A61B 5/6801 |

FOREIGN PATENT DOCUMENTS

| | | | | |
|---|---|---|---|---|
| JP | 4107813 B2 * | 6/2008 | ............. | A61B 5/022 |
| TW | 200640413 A | 12/2006 | | |
| TW | M557587 U | 4/2018 | | |
| WO | WO 2017/136772 A1 | 8/2017 | | |
| WO | WO-2018123385 A1 * | 7/2018 | ......... | A61B 5/02233 |

\* cited by examiner

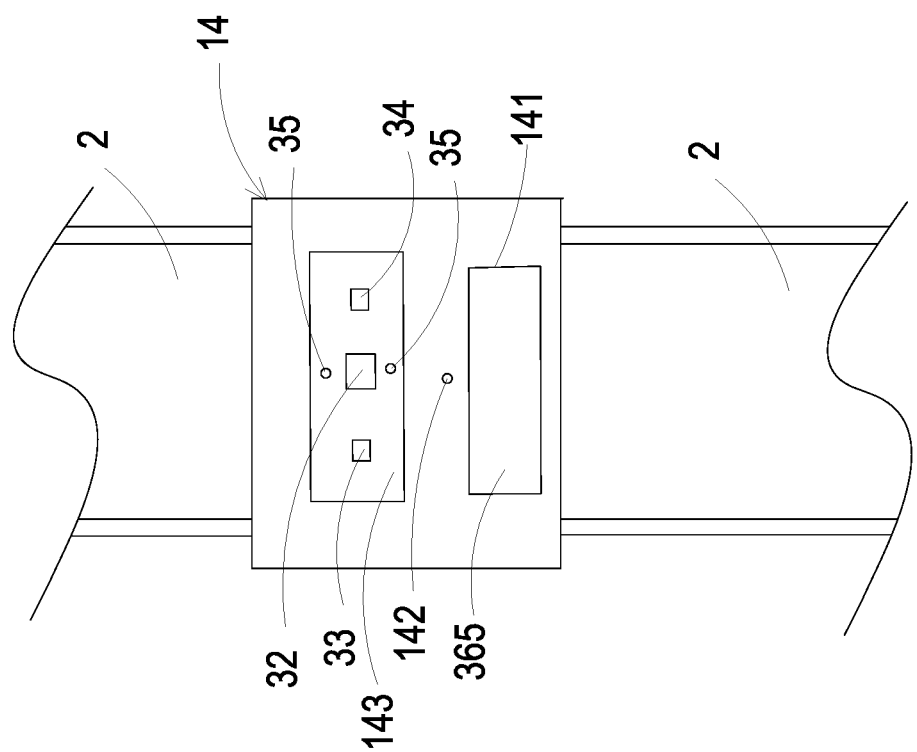

WEARABLE HEALTH MONITORING DEVICE

FIELD OF THE INVENTION

The present disclosure relates to a wearable device, and more particularly to a wearable health monitoring device having a biometric monitoring module for performing a health measurement and implementing an optical blood pressure measurement combined with an inflatable blood pressure measurement.

BACKGROUND OF THE INVENTION

Nowadays, the pursuit of efficiency and the personal pressure are growing and the awareness of the pursuit of personal health is gradually developing. Thus, the ordinary people will want to regularly monitor or examine their own health conditions. In general, the conventional data measurement of human physiological health information is mainly obtained through a fixed sphygmomanometer or a large-scale detection instrument, which usually includes components such as a motor-driven gas pump, an airbag, a sensor and a pressure-releasing valve and a battery. The motor-driven gas pump is prone to generate the frictional loss, and the assembled components thereof are bulky. It is not conducive to regular use. Moreover, if a miniature-sized motor-driven gas pump is used, the frictional loss will be increased and more energy will be consumed.

In order to facilitate the ordinary people to regularly monitor their own health conditions and allow the monitoring device to be carried easily, more and more wearable health monitoring devices are introduced into the market. In view of the common wearable health monitoring devices on the market, they are used for measuring the health conditions by an optical detection method. However, the precision of the optical detection method is not high enough and it often results in an error value to be generated. Reliable data cannot be obtained effectively. As a result, the users cannot obtain accurate and relevant data about their health, so that the users may misjudge their health conditions. Generally speaking, in order to measure physiological information of a person to be tested, a specified position such as the head, the heart part, the wrist or the ankle is usually selected to be monitored. The positions mentioned above are the most sensible in the human body for monitoring information such as pulse blood pressure and heartbeat. By monitoring at the positions, the physiological health information of the person to be tested can be understood quickly and effectively. However, as mentioned above, if the wearable health monitoring device with the optical detection method is used, the precision of the optical detection method is not high enough so that the measured data is usually not reliable. If the commercially-available sphygmomanometers or other measuring instruments with higher reliability are used, the instruments have bulky volume and fail to meet the requirements of light weightiness, thinning and easy portability.

Therefore, there is a need of providing a wearable health monitoring device to address the above-mentioned issues. The wearable health monitoring device is small-sized, miniaturized, portable, power-saving, high-precise and facilitated for personal health monitoring device.

SUMMARY OF THE INVENTION

An object of the present disclosure is to provide a wearable health monitoring device. The wearable health monitoring device includes a biometric monitoring module embedded in the monitoring main-body for performing the health measurement, and a photoelectric sensor for perform the optical blood pressure measurement. The combination of a barometric blood pressure meter and a pressure sensor is utilized to implement an inflatable blood pressure measurement. The health data information monitored by the inflatable blood pressure measurement is utilized as the basis for correction of the optical blood pressure measurement before the optical blood pressure measurement is performed. Thus, it makes the measurement more reliable, accurate and capable of being performed at anytime and anywhere. Moreover, the health data information can be further transmitted to an external link device by a control module to store and record for further analysis and statistics. Thus, the health condition of the wearer can be understood well and informed immediately, and the rescue treatment can be further provided.

In accordance with an aspect of the present disclosure, a wearable health monitoring device is provided and includes a monitoring main-body, a wearable component and a biometric monitoring module. The monitoring main-body includes an embedding seat, a monitoring-zone slot and a cover plate. The embedding seat has an embedding slot portion concavely formed and a bottom of the embedding slot portion is in fluid communication with a gas-flow slot and an exhausting channel. The monitoring-zone slot is adjacent to a side of the embedding seat. The cover plate covers the bottom of the embedding slot portion and has a slot opening passing therethrough and spatially corresponding to a position of the gas-flow slot, an exhausting aperture passing therethrough and spatially corresponding to a position of the exhausting channel and a transparent mask spatially corresponding to a position of the monitoring-zone slot. The wearable component is connected to an outside of the monitoring main-body. The biometric monitoring module is disposed within the monitoring main-body and includes a photoelectric sensor, a pressure sensor and an air-pressure-based blood pressure meter. The photoelectric sensor and the pressure sensor are disposed and positioned in the monitoring-zone slot to perform monitoring. The air-pressure-based blood pressure meter is embedded and positioned in the embedding slot portion of the embedding seat. The air-pressure-based blood pressure meter includes a gas-collecting actuator and an elastic air-bag. The elastic air-bag is compressed and disposed in the gas-flow slot of the embedding slot portion and the slot opening of the cover plate. The gas-collecting actuator transports a gas to the elastic air-bag, and the elastic air-bag is inflated and elastically protrudes out of the cover plate. Consequently, the elastic air-bag is attached to a skin tissue of a wearing user, and the pressure sensor measures vasoconstriction pulsation under the skin tissue and generates a detection signal accordingly. The detection signal is converted into health data information and is outputted, wherein the health data information is provided to the photoelectric sensor for calibrating a calculation of detection thereof to output precise health data information.

In accordance with another aspect of the present disclosure, a wearable health monitoring device is provided and includes a monitoring main-body, a wearable component and a biometric monitoring module. The monitoring main-body includes an embedding seat, a monitoring-zone slot and a cover plate. The embedding seat has an embedding slot portion concavely formed and a bottom of the embedding slot portion is in fluid communication with a gas-flow slot and an exhausting channel. An air-bag channel is disposed on a side of the embedding seat and in fluid communication with the gas-flow slot. The monitoring-zone slot is adjacent to a side of the embedding seat. The cover plate covers the bottom of the embedding slot portion and has an exhausting aperture passing therethrough and spatially corresponding to a position of the exhausting channel and a transparent mask spatially corresponding to a position of the monitoring-zone slot. The wearable component is connected to an outside of the monitoring main-body. An elastic air-bag is disposed around an inner annulus of the wearable component and includes an inlet end embedded and fixed in the air-bag channel of the embedding seat. The biometric monitoring module is disposed within the monitoring main-body and includes a photoelectric sensor, a pressure sensor and an air-pressure-based blood pressure meter. The photoelectric sensor and the pressure sensor are disposed and positioned in the monitoring-zone slot to perform monitoring. The air-pressure-based blood pressure meter is embedded and positioned in the embedding slot portion of the embedding seat. The air-pressure-based blood pressure meter includes a gas-collecting actuator, a gas-collector seat, a chamber plate and a valve membrane. The gas-collector seat includes a gas-collecting slot, and the gas-collecting slot is in fluid communication with the gas-flow slot of the embedding seat and the air-bag channel. The gas-collecting actuator transport a gas from the gas-collecting slot to the elastic air-bag through the air-flow slot and the air-bag channel, and the elastic air-bag is inflated and elastically protrudes out of the inner annulus of the wearable component. Consequently, the elastic air-bag is attached to a skin tissue of a wearing user, and the pressure sensor measures vasoconstriction pulsation under the skin tissue and generates a detection signal accordingly. The detection signal is converted into health data information and is outputted. The health data information is provided to the photoelectric sensor for calibrating a calculation of detection thereof to output precise health data information.

The above contents of the present disclosure will become more readily apparent to those ordinarily skilled in the art after reviewing the following detailed description and accompanying drawings, in which:

BRIEF DESCRIPTION OF THE DRAWINGS

FIG. 2B is a rear view illustrating the monitoring main-body of the wearable health monitoring device according to the embodiment of the present disclosure;

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
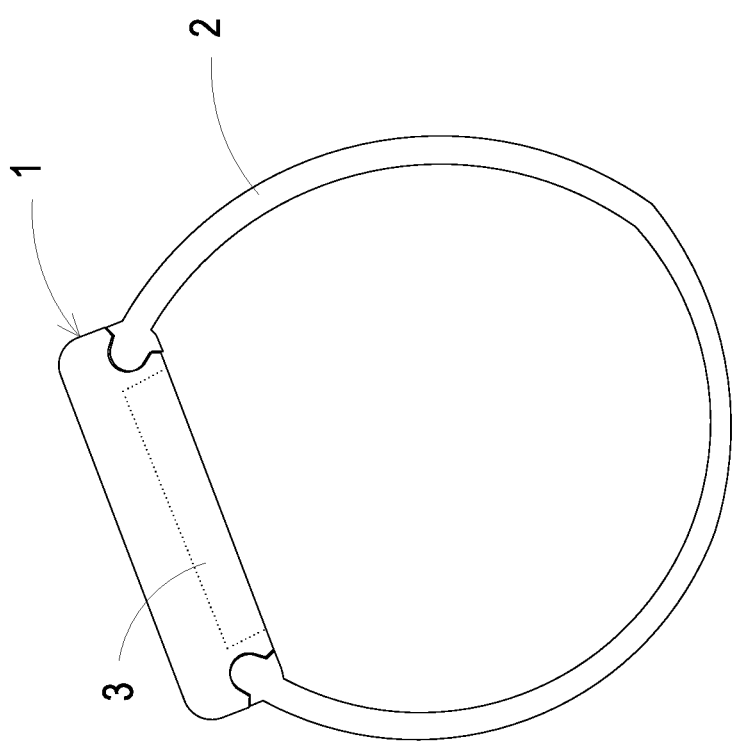
FIG. 1 is a schematic structural view illustrating a wearable health monitoring device according to an embodiment of the present disclosure.
Figure 2A:
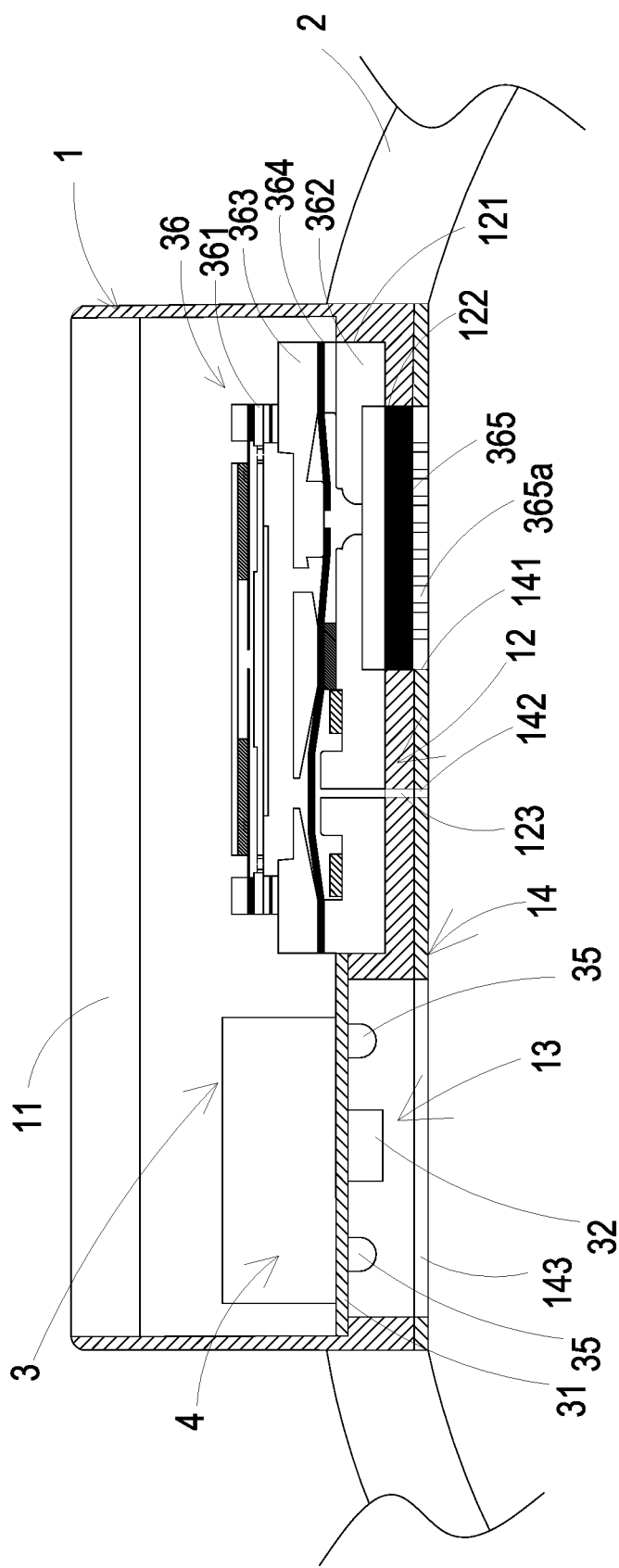
FIG. 2A is a cross sectional view illustrating the wearable blood pressure measuring device having the biometric monitoring module according the embodiment of the present disclosure.

Please refer to FIGS. 1, 2A and 2B. The present discourse provides a wearable health monitoring device for a user to wear on the wrist for health monitoring. In the embodiment, the wearable health monitoring device includes a monitoring main-body 1, a wearable component 2, a biometric monitoring module 3 and a control module 4.

In the embodiment, the wearable component 2 can be for example but not limited to a ring-shaped strip structure composed of a soft or rigid material, such as a silicone material, a plastic material, a metal material or other related materials. The present disclosure is not limited thereto. Preferably but not exclusively, the wearable component 2 is mainly used to wrap around a specific part of the wearing user, such as a wrist or an ankle. As to the connection manner of the two ends of the wearable component 2, the attaching means of the touch fasteners is applied. In an embodiment, the fastening means of the convex-and-concave butt joints, or the buckle ring commonly used for the general wearable component is applied. In other embodiment, the wearable component 2 may be a ring structure formed in one piece. The connection manner is adjustable according to the practical requirements. The present disclosure is not limited thereto.

In the embodiment, the monitoring main-body 1 includes a screen 11, an embedding seat 12, a monitoring-zone slot 13 and a cover plate 14. The screen 11 is disposed on a top surface of the monitoring main-body 1 to display health information, but not limited thereto. In the embodiment, the screen 11 can be for example but not limited to a touch screen, and the wearing user can touch the screen 11 to select the information to be displayed. Preferably but not exclusively, the information is at least one selected from the group consisting of the health information of the wearing user, the time information and the caller ID information. In the embodiment, the embedding seat 12 is disposed on a bottom of the monitoring main-body 1, and has an embedding slot portion 121 concavely formed. A bottom of the embedding slot portion 121 is in fluid communication with a gas-flow slot 122 and an exhausting channel 123. The monitoring-zone slot 13 is disposed on the bottom of the monitoring main-body 1 and adjacent to a side of the embedding seat 12. The cover plate 14 covers the bottom of the embedding slot portion 121. In the embodiment, the cover plate 14 has a slot opening 141, an exhausting aperture 142 and a transparent mask 143. The slot opening 141 passes through the cover plate 14 and spatially corresponds to a position of the gas-flow slot 122. The exhausting aperture 142 passes through the cover plate 14 and spatially corresponds to a position of the exhausting channel 123. The transparent mask 143 spatially corresponds to a position of the monitoring-zone slot 13.

Figure 3:
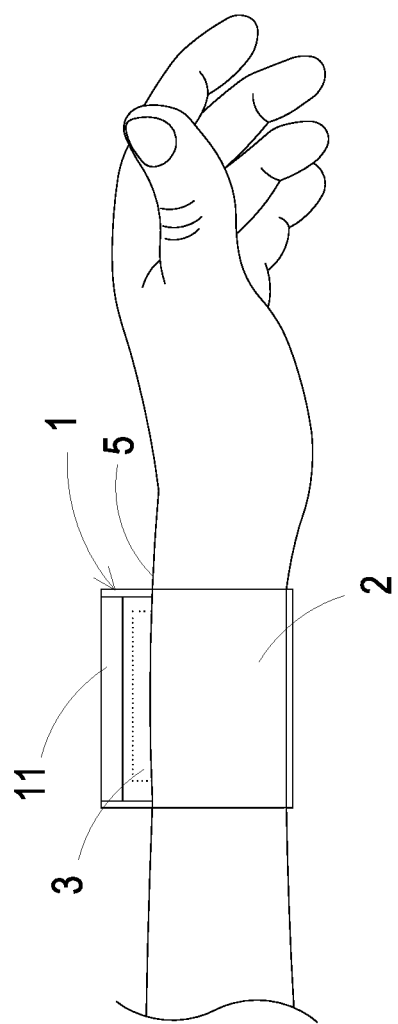
FIG. 3 shows the wearable health monitoring device of the present disclosure worn on a user.

Please refer to FIGS. 2A, 2B and 3. In the embodiment, the biometric monitoring module 3 is disposed within the monitoring main-body 1 and includes a driving circuit board 31, a photoelectric sensor 32, a pressure sensor 33, an impedance sensor 34, at least one light-emitting element 35 and an air-pressure-based blood pressure meter 36. The driving circuit board 31 is disposed and positioned in the monitoring-zone slot 13. The photoelectric sensor 32, the pressure sensor 33, the impedance sensor 34 and the at least one light-emitting element 35 are packaged and positioned under the driving circuit board 31 and in connection with the driving circuit board 31, so that the driving circuit board 31 provides a required electrical connection and wire conduction for driving-control signals. In the embodiment, the driving circuit board 31 also provides the air-pressure-based blood pressure meter 36 with the electrical connection and the control of the driving-control signal. The photoelectric sensor 32, the pressure sensor 33, the impedance sensor 34 and each of the light-emitting elements 35 are disposed and positioned under the driving circuit board 31 for monitoring purposes. The transparent mask 143 of the cover plate 14 covers and seals the monitoring-zone slot 13. Consequently, the photoelectric sensor 32, the pressure sensor 33, the impedance sensor 34 and each of the light-emitting elements 35 are protectively covered and dustproof. Besides, the transparent mask 143 is transparent for the purpose of measuring the skin tissue of the wearing user, and the photoelectric sensor 32 (or any other light-related sensor) may receive the reflected light from the skin tissue 5 and generates a detection signal. In the embodiment, the control module 4 is packaged on the driving circuit board 31, for providing the photoelectric sensor 32, the pressure sensor 33, the impedance sensor 34, each of the light-emitting elements 35 and air-pressure-based blood pressure meter 36 with the electrical connection and the control of the driving signal, and further for receiving and outputting the health data information. When the photoelectric sensor 32 is attached to the skin tissue 5 of the wearing user, a light emitted from the light-emitting element 35 passes through the transparent mask 142 and further irradiates the skin tissue 5. The light reflected is received by the photoelectric sensor 32 to generate the detection signal. The detection signal is transmitted to the control module 4. The control module 4 converts the detection signal into the health data information to be outputted. The health data information measured by the photoelectric sensor 32 includes heart rate data information, electrocardiogram data information and blood pressure data information. The pressure sensor 33 of the biometric monitoring module 3 is attached to the skin tissue 5 of the wearing user to generate the detection signal and the detection signal is converted into the health data information and is outputted by the control module 4. The health data information measured by the pressure sensor 33 includes respiratory frequency data and blood pressure data information. The impedance sensor 34 of the biometric monitoring module 3 is attached to the skin tissue 5 of the wearing user to generate the detection signal and the detection signal is converted into the health data information and is outputted by the control module 4. The health data information measured by the impedance sensor 34 includes blood glucose data information.

Please refer to FIGS. 2A and 2B and FIG. 4A to 4D. In the embodiment, the air-pressure-based blood pressure meter 36 is embedded and positioned in the embedding slot portion 121 of the embedding seat 12. The air-pressure-based blood pressure meter 36 includes a gas-collecting actuator 361, a gas-collector seat 362, a chamber plate 363, a valve membrane 364 and an elastic air-bag 365. The gas-collector seat 362 is disposed on the embedding slot portion 121 and includes a gas-collecting slot 362a concavely formed on a bottom surface, which spatially corresponds to the gas-flow slot 122. The gas-collector seat 362 further includes a lower gas-collecting chamber 362b and a lower pressure-releasing chamber 362c formed on a top surface of the gas-collector seat 362. In the embodiment, a gas-collecting perforation 362d is formed and disposed between the gas-collecting slot 362a and the lower gas-collecting chamber 362b to allow the gas-collecting slot 362a and the lower gas-collecting chamber 362b to communicate with each other. The lower gas-collecting chamber 362b and the lower pressure-releasing chamber 362c are separated apart on the top surface of the gas-collecting seat 362. A communication channel 362e is disposed between the lower gas-collecting chamber 362b and the lower pressure-releasing chamber 362c to allow the lower gas-collecting chamber 362b and the lower pressure-releasing chamber 362c to communicate with each other. In the embodiment, a first protrusion 362f is formed in the lower pressure-releasing chamber 362b and a pressure-releasing perforation 362g is disposed at a center of the first protrusion 362f. The pressure-releasing perforation 362g is in fluid communication with the lower pressure-releasing chamber 362c and the exhausting aperture 142 of the cover plate 14. The elastic air-bag 365 is compressed and disposed on the gas-collecting slot 362a to cover and seal the gas-collecting slot 362a. Moreover, the elastic air-bag 365 is fixed in the gas-flow slot 122 of the embedding slot portion 121 and spatially corresponds to the slot opening 141 of the cover plate 14. The elastic air-bag 365 and the cover plate 14 are coplanar and the elastic air-bag 365 is maintained without protruding out of the cover plate 14. In the embodiment, the elastic air-bag 365 is in fluid communication with the gas-collecting slot 362a and the gas-collecting perforation 362d, so that the elastic air-bag 365 is capable of being inflated and elastically protruding out of the cover plate 14. The elastic air-bag 365 has a pressing plate 365a disposed on an inflatable end thereof to abut against and attach the skin tissue 5 of the wearing user. In the embodiment, the chamber plate 363 is carried and disposed on the gas-collecting seat 362. In the embodiment, the chamber plate 363 includes an upper gas-collecting chamber 363a and an upper pressure-releasing chamber 363b formed on a top surface spatially corresponding to the gas-collecting seat 362. The upper gas-collecting chamber 363a and the lower gas-collecting chamber 362b are matched and sealed with each other. The upper pressure-releasing chamber 363b and the lower pressure-releasing chamber 362c are matched and sealed with each other. A second protrusion 363c is formed in the upper gas-collecting chamber 363a, and a communication chamber 363d is concavely formed on a bottom surface of the chamber plate 363 opposite to the upper gas-collecting chamber 363a and the upper pressure-releasing chamber 363b. The gas-collecting actuator 361 is carried and disposed on the chamber plate 363 to seal and cover the communication chamber 363d, and at least one communication aperture 363e communicates with the communication chamber 363d and is in fluid communication with the upper gas-collecting chamber 363a and the upper pressure-releasing chamber 363b. Moreover, the valve membrane 364 is disposed between the gas-collector seat 362 and the chamber plate 363 and abutted against the first protrusion 362f to seal the pressure-releasing perforation 362g. The valve membrane 364 has a valve aperture 364a disposed at a position abutted against the second protrusion 363c, and the valve aperture 364a is sealed by abutting against the second protrusion 363c.

Figure 5A:
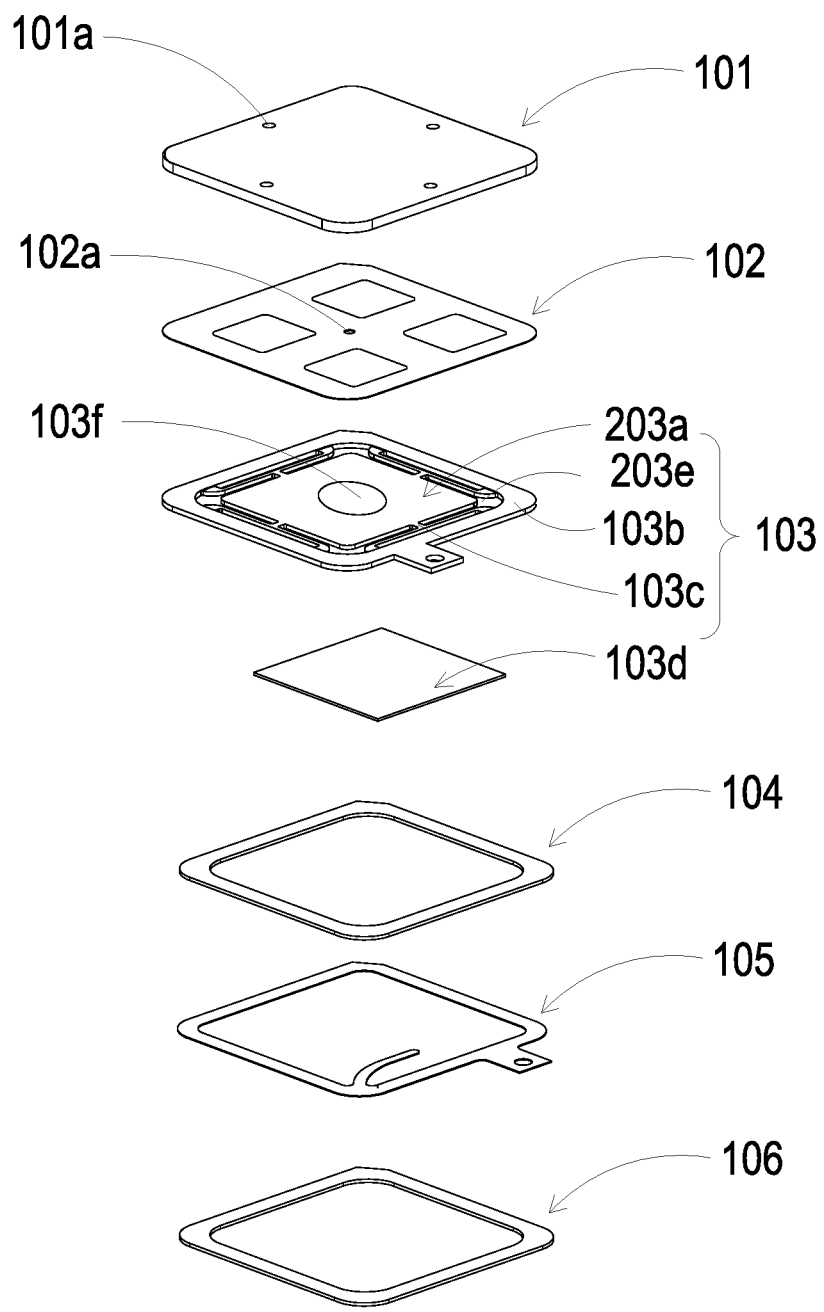
FIG. 5A is a disassembled structural view illustrating the micro pump of the wearable health monitoring device according to the embodiment of the present disclosure.
Figure 5B:
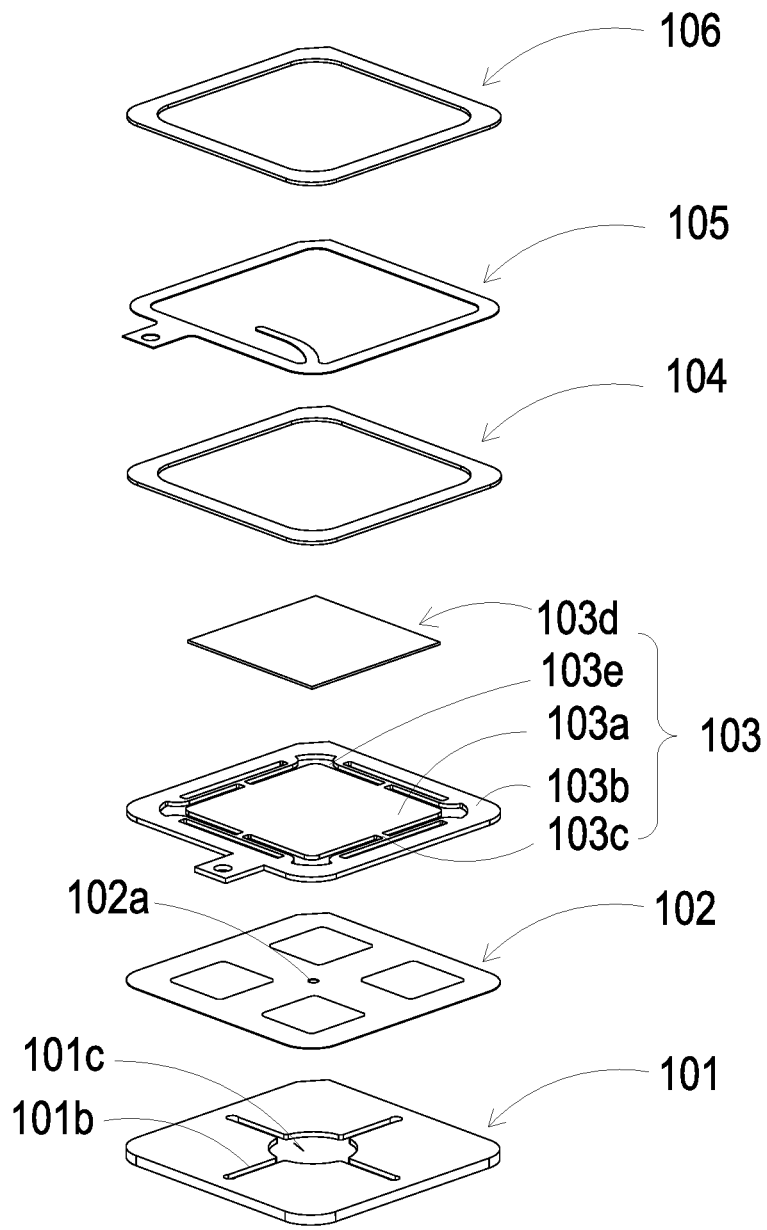
FIG. 5B is a disassembled structural view illustrating the micro pump of the wearable health monitoring device according to the embodiment of the present disclosure and taken from another perspective.

Please refer to FIGS. 5A and 5B. In the embodiment, the gas-collecting actuator 361 is a micro pump 10. The micro pump 10 includes a gas inlet plate 101, a resonance plate 102, a piezoelectric actuator 103, a first insulation plate 104, a conducting plate 105 and a second insulation plate 106. The gas inlet plate 101, the resonance plate 102, the piezoelectric actuator 103, the first insulation plate 104, the conducting plate 105 and the second insulation plate 106 are stacked sequentially. The gas inlet plate 101 has at least one inlet aperture 101a, at least one convergence channel 101b and a convergence chamber 101c. The inlet aperture 101a allows a gas to flow in. The convergence channel 101b is disposed correspondingly to the inlet aperture 101a and guides the gas from the inlet aperture 101a toward the convergence chamber 101c. In the embodiment, the number of the inlet apertures 101a and the number of the convergence channels 101b are the same. Preferably but not exclusively, there are four inlet apertures 101a and four convergence channels 101b. The four inlet apertures 101a are in fluid communication with the four convergence channels 101b, respectively, and the four convergence channels 101b guide the gas to the convergence chamber 101c.

Figure 6A:
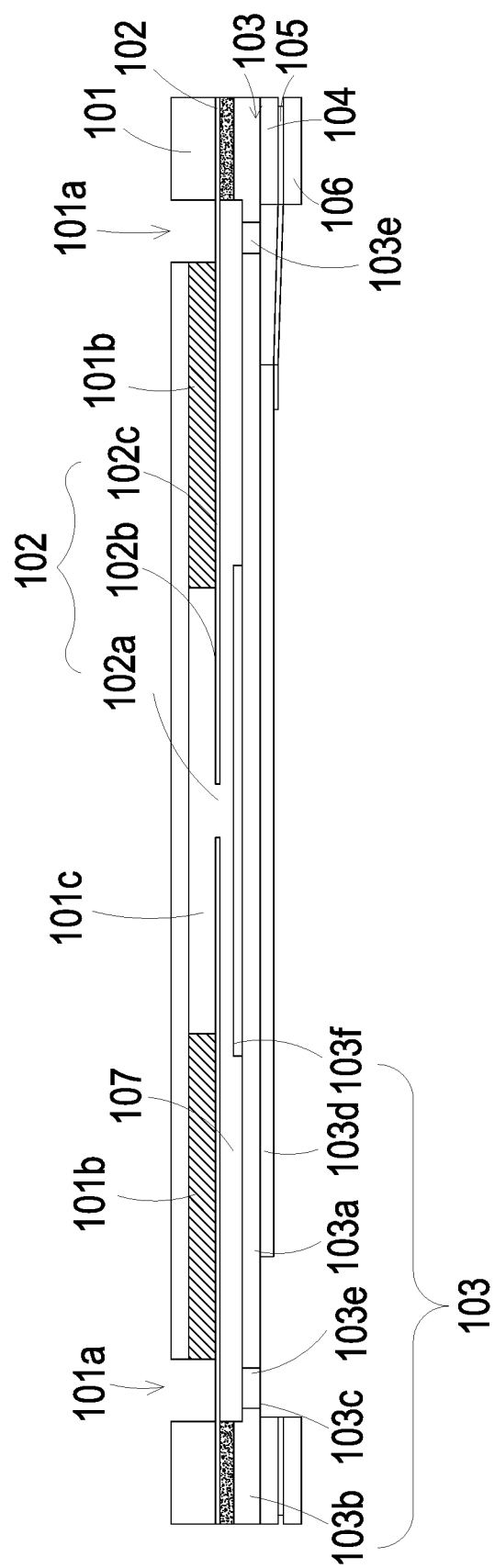
FIG. 6A is a cross sectional view illustrating the micro pump according to the embodiment of the present disclosure.

Please refer to FIGS. 5A, 5B and 6A. In the embodiment, the resonance plate 102 is assembled with the gas inlet plate 101 by means of adhesion. The resonance plate 102 has a central aperture 102a, a movable part 102b and a fixing part 102c. The central aperture 102a is disposed at a center of the resonance plate 102 and aligned with the convergence chamber 101c of the gas inlet plate 101. The movable part 102b surrounds the central aperture 102a and spatially corresponds to the convergence chamber 101c. The fixing part 102c is located at a peripheral portion of the resonance plate 102 and is attached on the gas inlet plate 101.

Please refer to FIGS. 5A, 5B and 6A. In the embodiment, the piezoelectric actuator 103 includes a suspension plate 103a, an outer frame 103, at least one bracket 103c, a piezoelectric element 103d, at least one vacant space 103e and a bulge 103f. Preferably but not exclusively, the suspension plate 103a is a square suspension plate. Compared with the design of the circular suspension plate, the square structure of the suspension plate 103a obviously has the advantage of power saving. Since the power consumption of the capacitive load operating at the resonant frequency is increased as the frequency is increased, and the resonance frequency of the suspension plate 103a in side-long square type is obviously lower than that of the circular suspension plate. The relative power consumption of the square suspension plate is obviously lower than that of circular suspension plate. Therefore, the suspension plate 103a is designed in a square type. Namely, the suspension plate 103a square-designed of the present disclosure is advantageous of power saving. In the embodiment, the outer frame 103b is arranged around the suspension plate 103a. The at least one bracket 103c is connected between the suspension plate 103a and the outer frame 103b for elastically supporting the suspension plate 103a. In the embodiment, a length of a side of the piezoelectric element 103d is smaller than or equal to a length of a side of the suspension plate 103a, and the piezoelectric element 103d is attached on a surface of the suspension plate 103a to drive the suspension plate 103a to undergo the bending vibration in response to an applied voltage. The at least one vacant space 103e is formed among the suspension plate 103a, the outer frame 103b and the bracket 103c to allow the gas flow therethrough. In the embodiment, the suspension plate 103a has a first surface and a second surface, and the bulge 103f is disposed on the second surface opposite to the first surface attached to the piezoelectric element 103d. In the embodiment, the bulge 103f is formed by an etching process, and a convex structure is formed on the second surface opposite to the first surface of the suspension plate 103a attached to the piezoelectric element 103d.

Please refer to FIGS. 5A, 5B and 6A. In the embodiment, the gas inlet plate 101, the resonance plate 102, the piezoelectric actuator 103, the first insulation plate 104, the conducting plate 105 and the second insulation plate 106 are stacked sequentially. A chamber space 107 is formed between suspension plate 103a and the resonance plate 102. Preferably but not exclusively, the chamber space 107 may be utilized a filler, for example but not limited to a conductive adhesive, to fill a gap generated between the resonance plate 102' and the outer frame 103b of the piezoelectric actuator 103, so that a specific depth between the resonance plate 102 and the suspension plate 103a can be maintained and thus the gas is introduced to flow more rapidly. Moreover, since the proper distance between the suspension plate 103a and the resonance plate 102 is maintained, the contact interference is reduced and the generated noise is largely reduced. In some embodiments, alternatively, the height of the outer frame 103b of the piezoelectric actuator 103 is increased, so that the thickness of the conductive adhesive filled within the gap between the resonance plate 102 and the outer frame 103b of the piezoelectric actuator 103 may be reduced. Thus, in the case where the suspension plate 103a' and the resonance plate 102 are maintained at a proper distance, the thickness of the conductive adhesive filled within the overall assembly of the micro pump 10 won't be affected by a hot pressing temperature and a cooling temperature, and it benefits to avoid that the conductive adhesive affects the actual size of the chamber space 107 due to the factors of thermal expansion and contraction after the assembly is completed. The present disclosure is not limited thereto. In addition, the transportation efficiency of the micro pump 10 is affected by the chamber space 107, so that the chamber space 107 maintained in a fixed size is important to provide stable transportation efficiency for the micro pump 10.

Figure 6B:
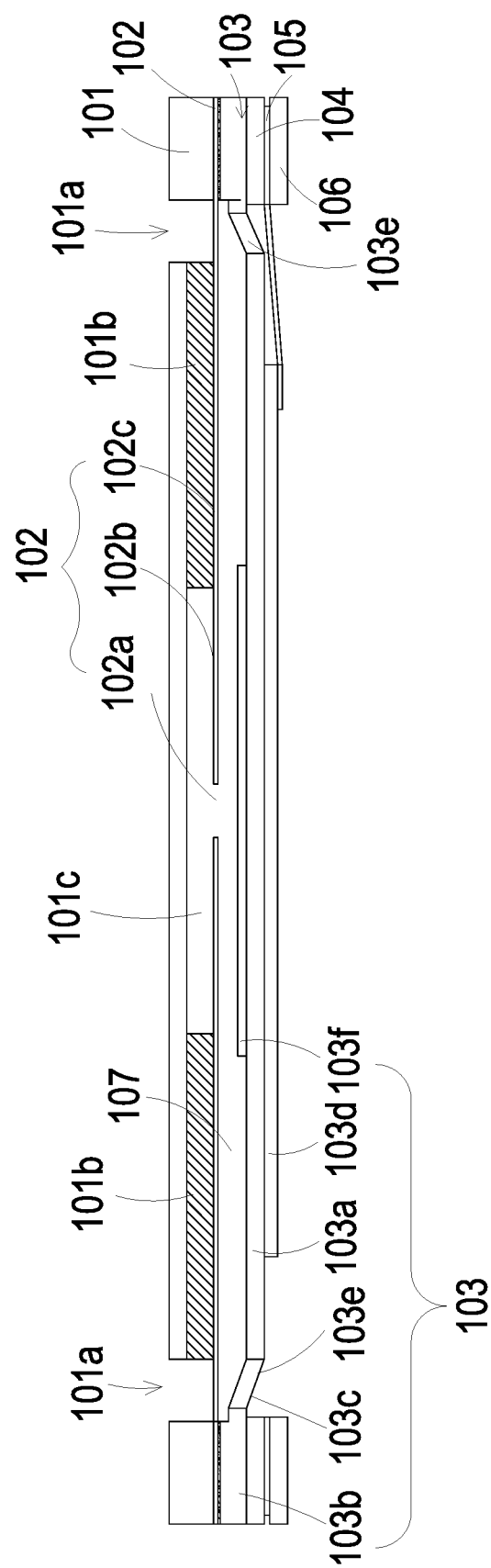
FIG. 6B is a cross sectional view illustrating the micro pump according to another embodiment of the present disclosure.

Please refer to FIG. 6B. In another exemplary structure of the piezoelectric actuator 103, the suspension plate 103a can be formed by a stamping method. The stamping method makes the suspension plate 103a extended outwardly at a distance, and the distance extended outwardly may be adjusted by the bracket 103c formed between the suspension plate 103a and the outer frame 103b, so that a surface of the bulge 103f on the suspension plate 103a is not coplanar with a surface of the outer frame 103b. A small amount of a filling material, for example a conductive adhesive, is applied to the assembly surface of the outer frame 103b to attach the piezoelectric actuator 103 on the fixing part 102c of the resonance plate 102 by means of hot pressing, so that the piezoelectric actuator 103 is assembled with the resonance plate 102. In this way, the entire structure may be improved by adopting the stamping method to form the suspension plate 103a of the piezoelectric actuator 103, thereby modifying the chamber space 107. A desired size of the chamber space 107 may be satisfied by simply adjusting the distance as described made by the stamping method. It simplifies the structural design for adjusting the chamber space 107. At the same time, it achieves the advantages of simplifying the process and saving the process time. In the embodiment, the first insulation plate 104, the conducting plate 105 and the second insulation plate 106 are all frame-shaped thin sheet, and stacked sequentially on the piezoelectric actuator 103 to obtain the entire structure of the micro pump 10.

Figure 6C:
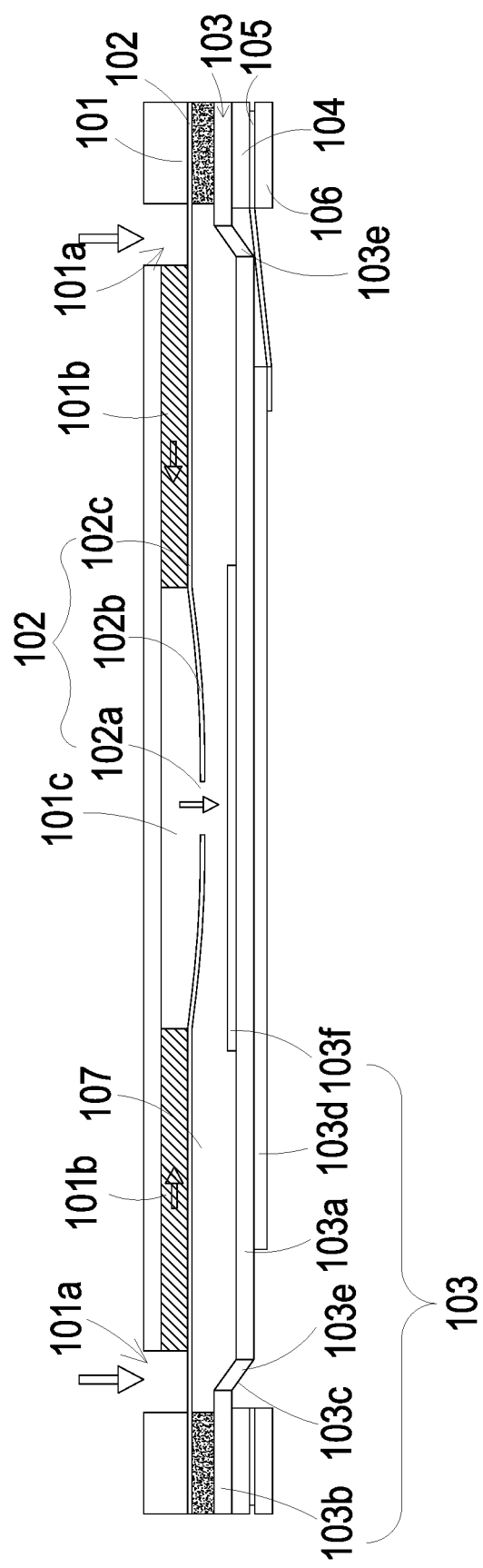
FIGS. 6C to 6E show the actions of the micro pump of FIG. 6A.
Figure 6D:
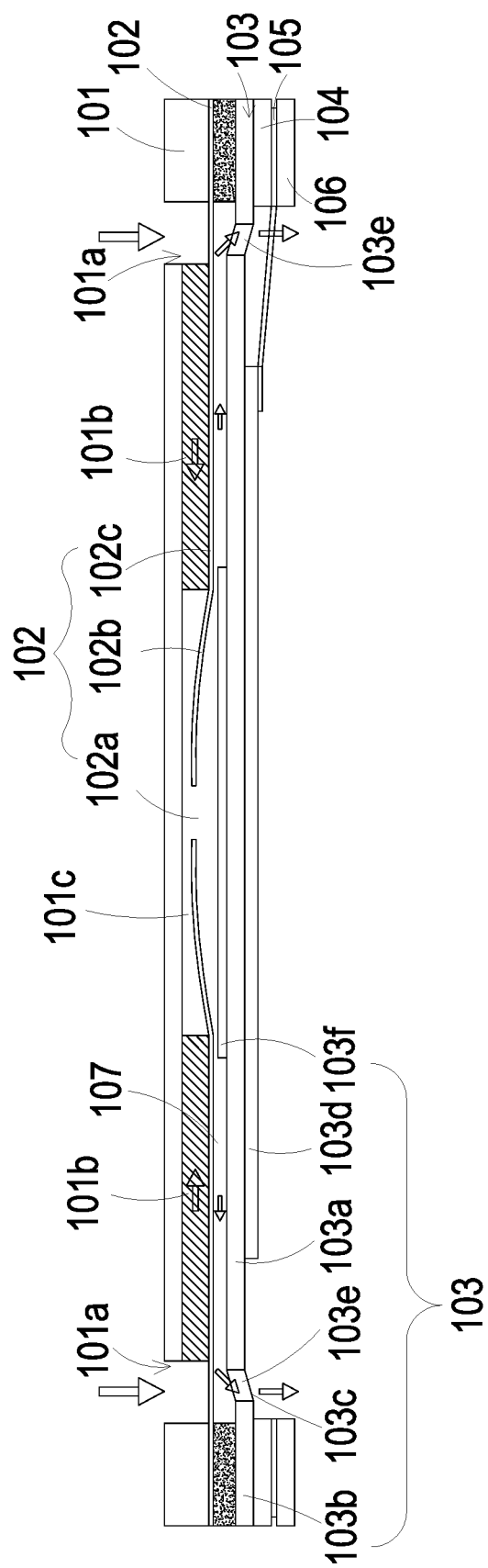
Figure 6E:
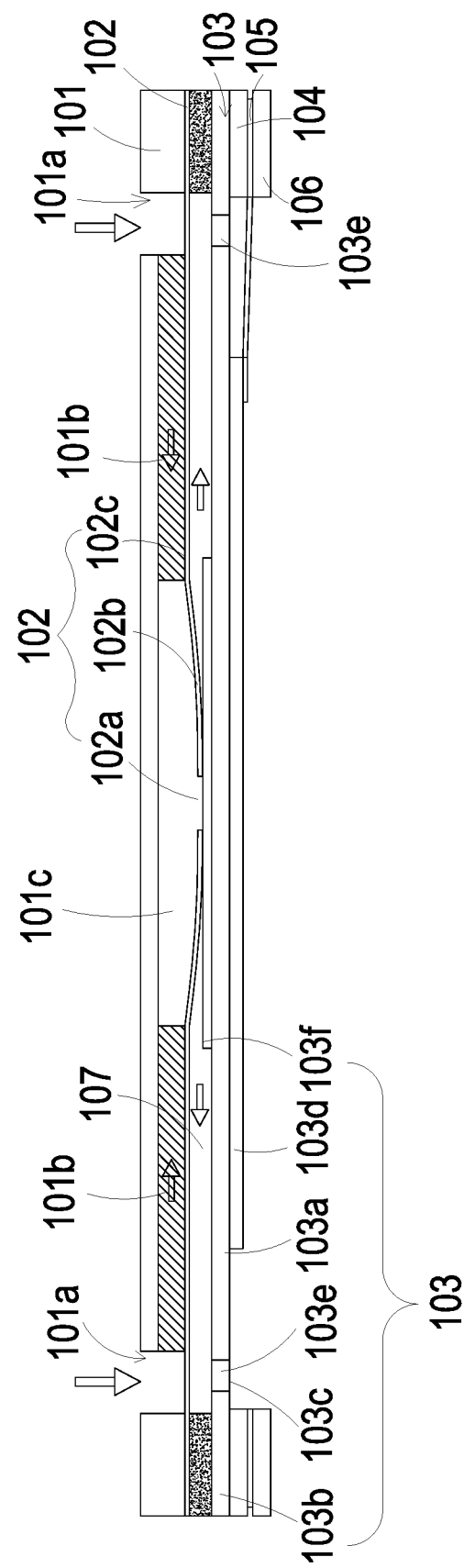

For describing the actions of the micro pump 10, please refer to FIGS. 6C to 6E. Firstly, as shown in FIG. 6C, when the piezoelectric element 103d of the piezoelectric actuator 103 is deformed in response to an applied voltage, the suspension plate 103a is displaced in a direction away from the gas inlet plate 101. In that, the volume of the chamber space 107 is increased, a negative pressure is formed in the chamber space 107, and the gas in the convergence chamber 101c is inhaled into the chamber space 107. At the same time, the resonance plate 102 is in resonance and thus displaced synchronously in the direction away from the gas inlet plate 101. Thereby, the volume of the convergence chamber 101c is increased. Since the gas in the convergence chamber 101c flows into the chamber space 107, the convergence chamber 101c is also in a negative pressure state, and the gas is sucked into the convergence chamber 101c by flowing through the inlet aperture 101a and the convergence channel 101b. Then, as shown in FIG. 6D, the piezoelectric element 103d drives the suspension plate 103a to be displaced toward the gas inlet plate 101 to compress the chamber space 107. Similarly, the resonance plate 102 is actuated by the suspension plate 103a (i.e., in resonance with the suspension plate 103a) and is displaced toward the gas inlet plate 101. Thus, the gas in the chamber space 107 is compressed synchronously and forced to be further transported through the vacant space 103e to achieve the effect of gas transportation. Finally, as shown in FIG. 6E, when the suspension plate 103a is vibrated back to the initial state, which is not driven by the piezoelectric element 103d, the resonance plate 102 is also driven to displace in the direction away from the gas inlet plate 101 at the same time. In that, the resonance plate 102 pushes the gas in the chamber space 107 toward the vacant space 103e, and the volume of the convergence chamber 101c is increased. Thus, the gas can continuously flow through the inlet aperture 101a and the convergence channel 101b and be converged in the confluence chamber 101c. By repeating the actions of the micro pump 10 shown in the above-mentioned FIGS. 6C to 6E continuously, the micro pump 10 can continuously transport the gas at a high speed to accomplish the gas transportation and output operations of the micro pump 10.

Please refer to FIG. 6A. In the embodiment, the gas inlet plate 101, the resonance plate 102, the piezoelectric actuator 103, the first insulation plate 104, the conducting plate 105 and the second insulation plate 106 are all produced by a micro-electromechanical surface micromachining technology. Thereby, the volume of the micro pump 10 is reduced and a microelectromechanical system of the gas pump 10 is constructed.

Figure 4A:
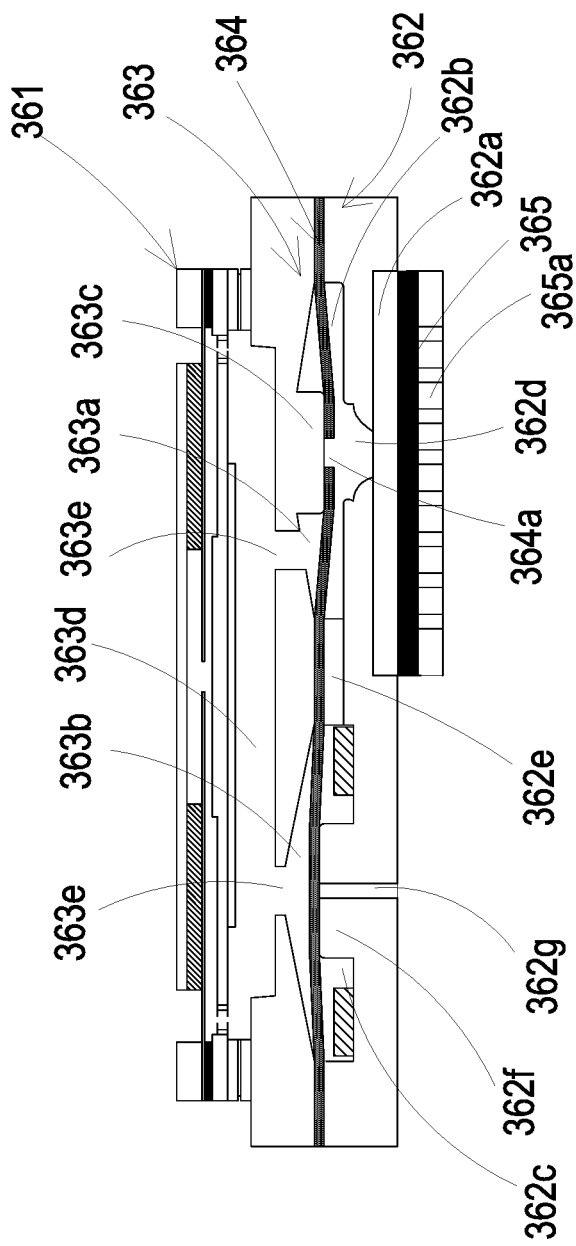
FIG. 4A is a cross sectional view illustrating the air-pressure-based blood pressure meter according to the embodiment of the present disclosure.
Figure 4B:
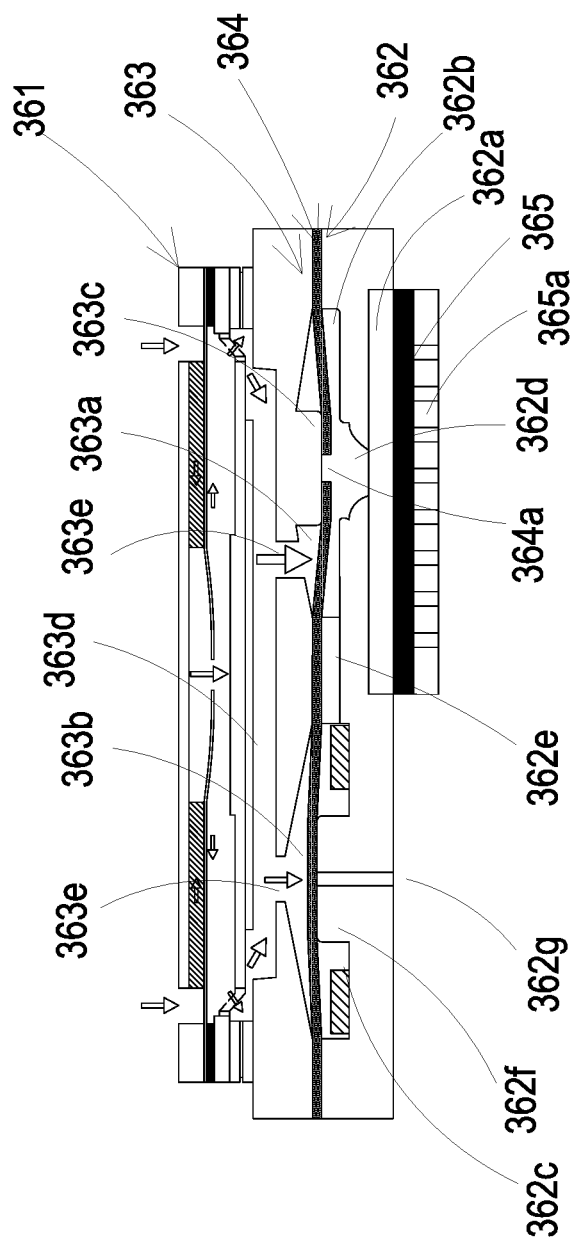
FIG. 4B to FIG. 4C are cross sectional views illustrating the air-pressure-based blood pressure meter of FIG. 4A performed in an inflating operation.
Figure 4C:
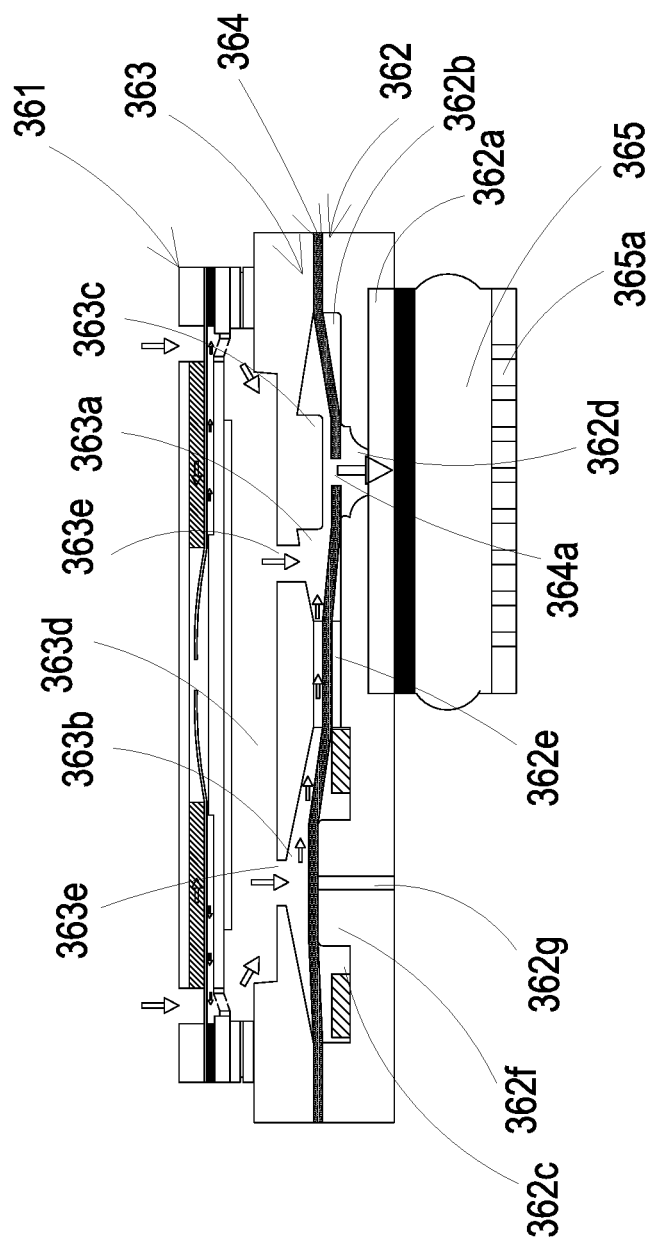
Figure 4D:
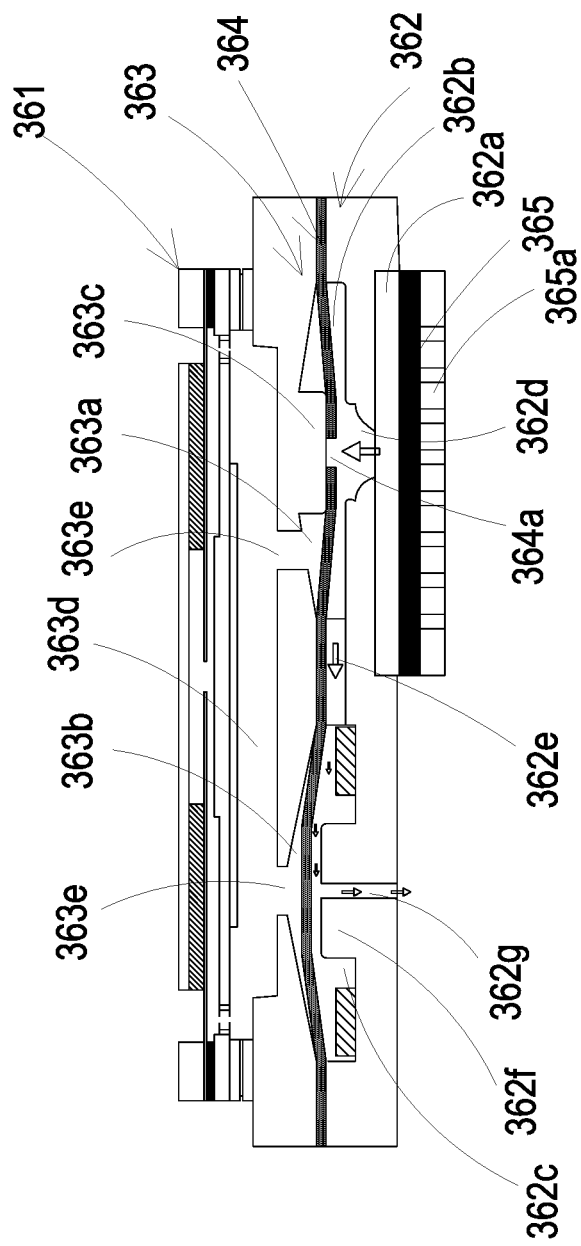
FIG. 4D is a cross sectional views illustrating the air-pressure-based blood pressure meter of FIG. 4A performed in a pressure-releasing operation.
Figure 7:
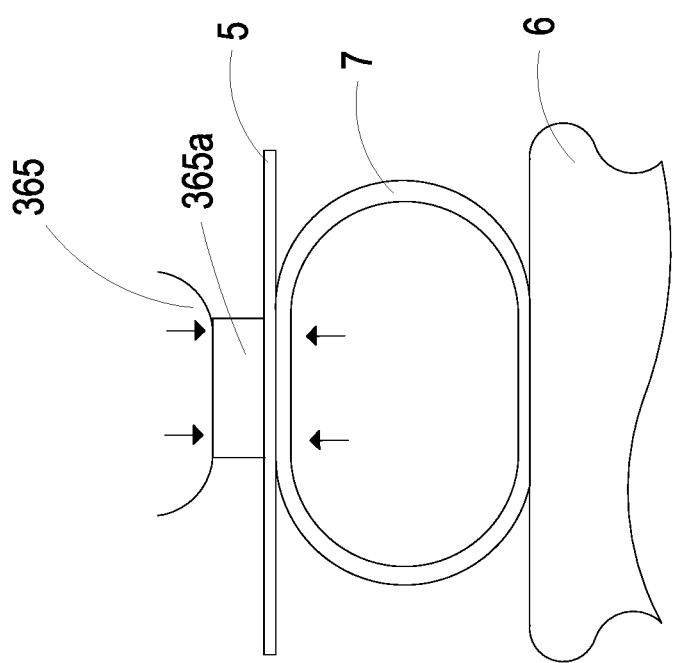
FIG. 7 shows a measuring action of the wearable health monitoring device according to the embodiment of the present disclosure.

According to the above descriptions, the air-pressure-based blood pressure meter 36 is implemented as shown in FIGS. 4B and 4C. When the gas-collecting actuator 361 is controlled and driven to transport a gas, the gas is inhaled from outside of the gas-collecting actuator 361 and transported to the communication chamber 363d, and then the gas is transported from the communication chamber 363d to the upper gas-collecting chamber 363a and the upper pressure-releasing chamber 363b through the communication aperture 363e. Consequently, the valve membrane 364 is pushed to move apart from the second protrusion 363c. The valve membrane 364 is pushed to abut against the first protrusion 362f and to seal the pressure-releasing perforation 362g. Moreover, the gas in the upper pressure-releasing chamber 363b is transported into the upper gas-collecting chamber 363a through the communication channel 362e and further transport into the lower gas-collecting chamber 362b of the gas-collector seat 362 through the valve aperture 364a of the valve membrane 364. In that, the gas is converged to the elastic air-bag 365 in fluid communication with the gas-collecting perforation 362d, and the elastic air-bag 365 is inflated and elastically protrudes out of the cover plate 14. Certainly, after the elastic air-bag 365 is inflated for a period of time, as shown in FIG. 7, the pressing plate 365a of the elastic air-bag 365 is attached to the skin tissue 5 of the wearing user. In this way, the blood vessel 7 between the skin tissue 5 and the bone 6 of the wearing user is pressed to stop blood flow. After the elastic air-bag 365 is inflated for the period of time and the inflation operation is stopped, as shown in FIG. 4D, the gas-collecting actuator 361 stops transporting gas. Under this circumstance, the gas pressure inside the elastic air-bag 365 is greater than that of the communication chamber 363d. The gas converged in the elastic air-bag 365 pushes the valve membrane 364 to move and abut against the second protrusion 363c, the valve aperture 364a is sealed, and the gas pushes the valve membrane 364 to move apart from the first protrusion 362f to open the pressure-releasing perforation 362g. The gas converged in the elastic air-bag 365 is transported to the pressure-releasing perforation 362g and discharged out of the air-pressure-based blood pressure meter 36, so that a pressure-releasing operation of the elastic air-bag 365 is performed. During the pressure-releasing process, the pressure of the blood vessel 7 is gradually reduced, and the pressure sensor 33 is operated to scan and measure. Namely, the blood vessel pulsation is measured by pressing and scanning, and an inflatable blood pressure monitoring operation is completed. It is a sensible measurement of blood pressure, and the blood pressure data can be measured more accurately.

In the embodiment, the photoelectric sensor 32 is utilized in the wearable health monitoring device of the present disclosure to receive the light, which is emitted from the light-emitting element 35 and reflected from the skin tissue, so that the detection signal is generated. In that, the measurement based on the photoplethysmogram (PPG) principle is achieved. The detection signal is transmitted to the control module 4 and is converted into the health data information for output. The health data information measured by the photoelectric sensor 32 includes heart rate data information, electrocardiogram data information and blood pressure data information. The optical measurement is also a way to achieve blood pressure measurement. Although the optical measurement can be performed every minute and every second, the health data information obtained therefrom is calculated by algorithm, but not obtained directly by the inflatable measurement. The measured result is not accurate enough. Therefore, the wearable health morning device of the present disclosure includes the air-pressure-based blood pressure meter 36 combined with the pressure sensor 33, which are minimized and suitable for the wearable device. The inflatable measurement for the blood pressure data information can be achieved and the measured result is more accurate. Furthermore, the measured result is utilized in an initial correction of the photoelectric measurement blood pressure, and an auxiliary confirmation of heart rate variability (HRV) and atrial fibrillation (AF). More specifically, before the photoelectric sensor 32 is performed for a first measurement, the air-pressure-based blood pressure meter 36 combined with pressure sensor 33 may be utilized to perform the inflatable measurement for the pressure data information. The health data information obtained from the inflatable measurement is provided to the photoelectric sensor 32 for the purpose of calibration. The photoelectric sensor 32 calibrates the optical measurement on the basis of the health data information obtained from the inflatable measurement. Thus, each detection signal generated from the photoelectric sensor 32 is calibrated, so as to output precise health data information. In addition, when the wearer has an accident, such as a fall or an abnormal blood glucose or blood oxygen detected, the air-pressure-based blood pressure meter 36 of the wearable health monitoring device of the present disclosure can be used together with the pressure sensor 33 to implement the inflatable blood pressure measurement. Thus, more reliable data is provided as reference to understand the user's health condition in the accident. Anyone who checks the wearable health monitoring device can be informed of the health data information immediately and the proper rescue treatment can be further provided. The wearable health monitoring device of the present disclosure is highly industrially utilized.

Figure 8:
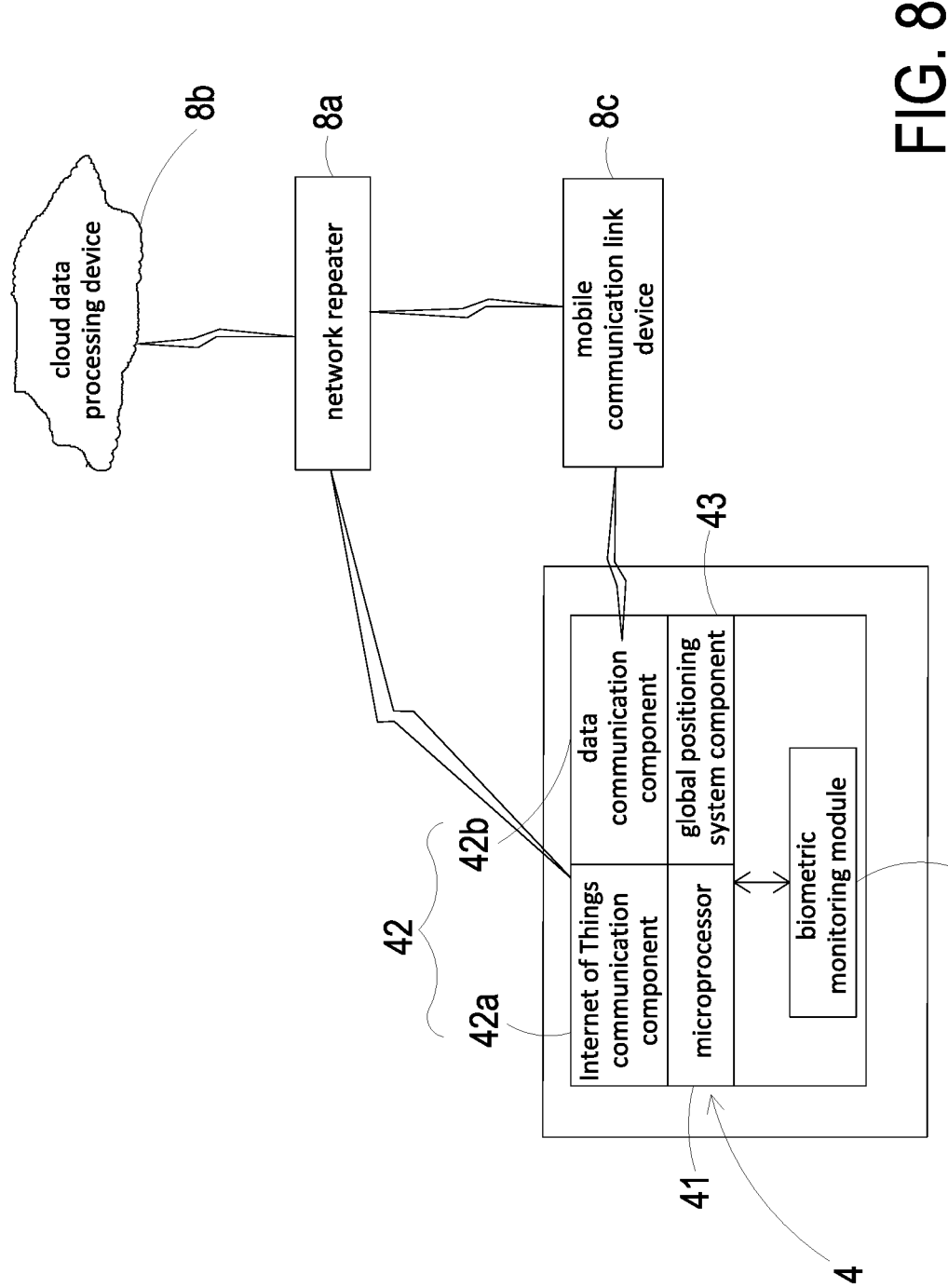
FIG. 8 shows a link transmission of the control module according to the embodiment of the present disclosure.

Please refer to FIG. 8. The wearable health morning device of the present disclosure includes the control module 4. In the embodiment, the control module 4 includes a microprocessor 41, a communicator 42 and a global positioning system component 43. The detection signals of the photoelectric sensor 32, the pressure sensor 33 and the impedance sensor 34 are converted into the health data information to output by the microprocessor 41. Preferably but not exclusively, the health data information is outputted and displayed on the screen 11 directly. Alternatively, the health data information is transmitted to the communicator 42. In the embodiment, the communicator 42 includes an Internet of Things (IoT) communication component 42a and a data communication component 42b. The Internet of Things communication component 42a receives the health data information from the biometric monitoring module 3 and transmits the health data information to an external link device to store and record for further analysis and statistics, so as to know the health condition of the wearing user better. The Internet of Things communication component 42a is a narrowband Internet of Things device transmitting a transmission signal by a narrowband radio communication technology. The external link device includes a network repeater 8a and a cloud data processing device 8b. In the embodiment, the Internet of Things communication component 42a transmits the health data information to the cloud data processing device 8b to store and record through the network repeater 8a for further analysis and statistics, so as to know the health condition of the wearing user. The data communication component 42b receives the health data information from the biometric monitoring module and transmits the health data information to the external link device to store and record for further analysis and statistics, so as to know the health condition of the wearing user better. The data communication component 42b transmits the health data information through a wireless communication transmission interface. The wireless communication transmission interface can be for example but not limited to a Wi-Fi module, a Bluetooth module, a radio frequency identification (RFID) module or a near field communication (NFC) module. The data communication component 42b transmits the health data information to the external link device and the external link device includes a mobile communication link device 8c. In the embodiment, the data communication component 42b transmits the health data information to the mobile communication link device 8c to store and record for further analysis and statistics, so as to know the health condition of the wearing user. The mobile communication link device 8c is at least one selected form the group consisting of a mobile phone device, a notebook computer and a tablet computer. Alternatively, the data communication component 42b receives the health data information from the biometric monitoring module 3 and transmits the health data information to the external link device. The external link device includes the mobile communication link device 8c, the network repeater 8a and the cloud data processing device 8b. The health data information is received by the mobile communication link device 8c and further transmitted to the cloud data processing device 8b to store and record for further analysis and statistics through the network repeater 8a, so as to know the health condition of the wearing user. The mobile communication link device 8c is at least one selected form the group consisting of a mobile phone device, a notebook computer and a tablet computer.

Figure 9:
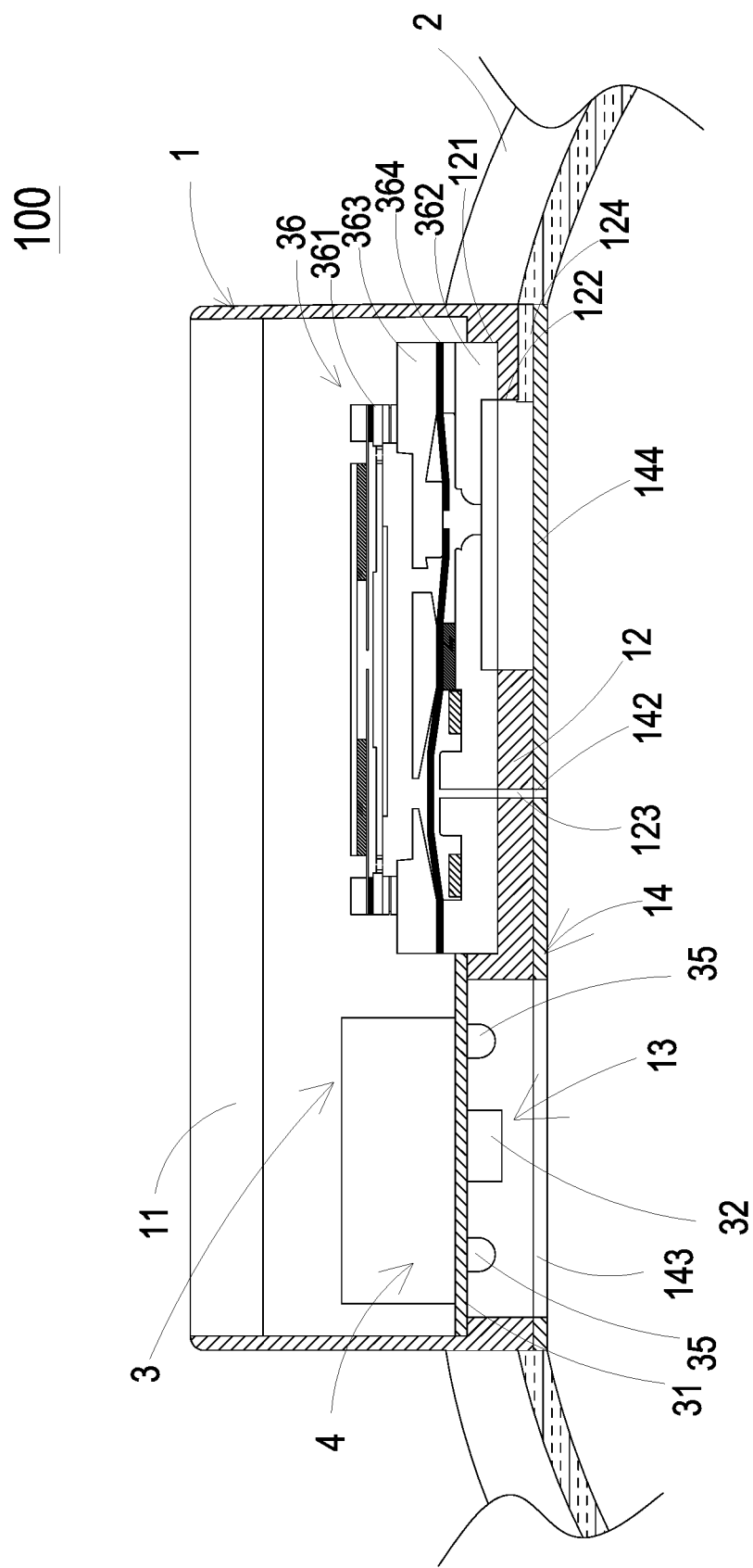
FIG. 9 is a cross sectional view illustrating the wearable health monitoring device having the elastic air-bag assembled according another embodiment of the present disclosure.
Figure 10:
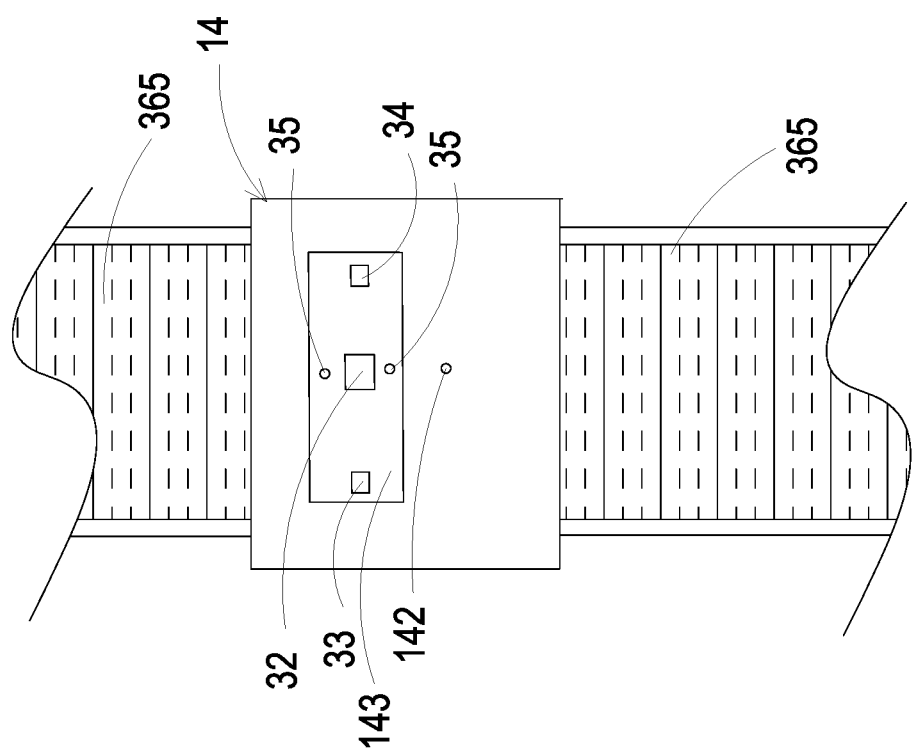
FIG. 10 is a rear view illustrating the monitoring main-body of the wearable health monitoring device having the elastic air-bag assembled on the wearable component according to another embodiment of the present disclosure.
Figure 11:
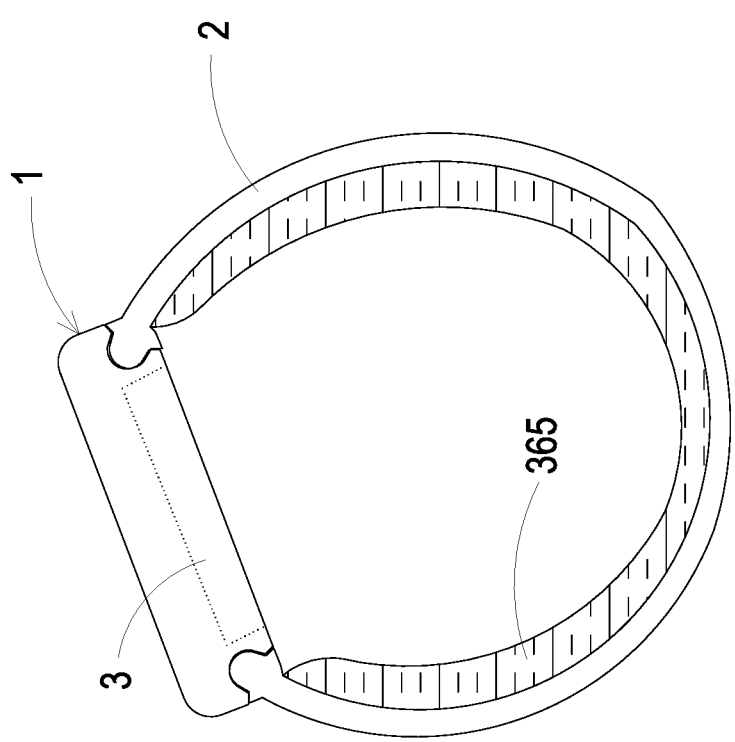
FIG. 11 is a schematic structural view illustrating the wearable health monitoring device having the elastic air-bag and assembled on the wearable component according to another embodiment of the present disclosure and inflated.

FIGS. 9, 10 and 11 show the wearable health monitoring device having the elastic air-bag 365 assembled according another embodiment of the present disclosure. In the embodiment, the elastic air-bag 365 is disposed around an inner annulus of the wearable component 2. An air-bag channel 124 is disposed on a side of the embedding seat 12 and in fluid communication with the air-flow slot 122. The elastic air-bag 365 includes an inlet end embedded and fixed in the air-bag channel 124. In the embodiment, the slot opening 141 of the cover plate 14 is omitted. The cover plate 14 includes a covering portion 144 to cover and seal the gas-flow slot 122 and the bottom of the air-bag channel 124. Consequently, the gas-flow slot 122 and the air-bag channel 124 form a flow channel in fluid communication with the elastic air-bag 365. In that, the gas is transported through the gas-flow slot 122 and introduced into the elastic air-bag 365 by the air-pressure-based blood pressure meter 36, so that the elastic air-bag 365 is inflated and elastically protrudes out of the inner annulus of the wearable component 2. Consequently, the elastic air-bag 365 abuts against the wrist of the wearing user, as shown in FIG. 7, the blood vessel 7 between the skin tissue 5 and the bone 6 of the wearing user is pressed to stop blood flow. Thereafter, the pressure sensor 33 is utilized to perform the inflatable blood pressure monitoring operation, so as to achieve the purpose of health monitoring.

In summary, the present disclosure provides a wearable health monitoring device. The wearable health monitoring device includes a biometric monitoring module embedded in the monitoring main-body for performing the health measurement, and a photoelectric sensor for perform the optical blood pressure measurement. The combination of a barometric blood pressure meter and a pressure sensor is utilized to implement an inflatable blood pressure measurement. The health data information monitored by the inflatable blood pressure measurement is utilized as the basis for correction of the optical blood pressure measurement before the optical blood pressure measurement is performed. Thus, it makes the measurement more reliable, accurate and capable of being performed at anytime and anywhere. Moreover, the health data information can be further transmitted to an external link device by a control module to store and record for further analysis and statistics. Thus, the health condition of the wearer can be understood well and informed immediately, and the rescue treatment can be further provided. Therefore, the wearable health monitoring device of the present disclosure is highly industrially utilized, so as to file a patent application.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A wearable health monitoring device comprising:
  a monitoring main-body comprising an embedding seat, a monitoring-zone slot and a cover plate, wherein the embedding seat has an embedding slot portion concavely formed and a bottom of the embedding slot portion is in fluid communication with a gas-flow slot and an exhausting channel, wherein the monitoring-zone slot is adjacent to a side of the embedding seat, wherein the cover plate covers the bottom of the embedding slot portion and has a slot opening passing therethrough and spatially corresponding to a position of the gas-flow slot, an exhausting aperture passing therethrough and spatially corresponding to a position of the exhausting channel, and a transparent mask spatially corresponding to a position of the monitoring-zone slot;
  a wearable component connected to an outside of the monitoring main-body; and
  a biometric monitoring module disposed within the monitoring main-body and comprising a photoelectric sensor, a pressure sensor and an air-pressure-based blood pressure meter, wherein the photoelectric sensor and the pressure sensor are disposed and positioned in the monitoring-zone slot to perform monitoring, and the air-pressure-based blood pressure meter is embedded and positioned in the embedding slot portion of the embedding seat, wherein the air-pressure-based blood pressure meter comprises a gas-collecting actuator and an elastic air-bag, wherein the elastic air-bag is compressed and disposed in the gas-flow slot of the embedding slot portion and the slot opening of the cover plate, wherein the gas-collecting actuator transports a gas to the elastic air-bag, and the elastic air-bag is inflated and elastically protrudes out of the cover plate, whereby the elastic air-bag is capable of being attached to a skin tissue of a wearing user, and the pressure sensor is capable of measuring vasoconstriction pulsation under the skin tissue and generates a detection signal accordingly, wherein the detection signal is converted into health data information and is outputted, wherein the health data information is provided to the photoelectric sensor for calibrating a calculation of the detection signal thereof to output precise health data information.

2. The wearable health monitoring device according to claim 1, wherein the biometric monitoring module further comprises a driving circuit board, an impedance sensor and at least one light-emitting element, wherein the driving circuit board is disposed and positioned in the monitoring-zone slot, and the photoelectric sensor, the pressure sensor, the impedance sensor and the light-emitting element are packaged and positioned under the driving circuit board and in connection with the driving circuit board, so as to obtain required electricity and a driving-control signal therefor and be utilized to measure at a position corresponding to the monitoring-zone slot, wherein the air-pressure-based blood pressure meter is electrically connected with the driving circuit board and a driving signal is provided by the driving circuit board, wherein the transparent mask of the cover plate covers and seals the monitoring-zone slot, so that the photoelectric sensor, the pressure sensor, the impedance sensor and the light-emitting element are protectively covered and dustproof, and the transparent mask is transparent for the purpose of measuring the skin tissue of the wearing user.

3. The wearable health monitoring device according to claim 2, wherein the photoelectric sensor of the biometric monitoring module is configured to transparently measures the skin tissue through a light emitted from the light-emitting element, and the light reflected is received by the photoelectric sensor to generate the detection signal and the detection signal is converted into health data information and is outputted, wherein the health data information includes heart rate data information, electrocardiogram data information and blood pressure data information.

4. The wearable health monitoring device according to claim 2, wherein the pressure sensor of the biometric monitoring module is configured to be attached to the skin tissue of the wearing user to generate the detection signal and the detection signal is converted into the health data information and is outputted, wherein the health data information includes respiratory frequency data information and blood pressure data information.

5. The wearable health monitoring device according to claim 2, wherein the impedance sensor of the biometric monitoring module is configured to be attached to the skin tissue of the wearing user to generate the detection signal and the detection signal is converted into health data information and is outputted, wherein the health data information includes blood glucose data information.

6. The wearable health monitoring device according to claim 1, wherein the air-pressure-based blood pressure meter further comprises a gas-collector seat, a chamber plate and a valve membrane, wherein the gas-collector seat is disposed on the embedding slot portion and comprises a gas-collecting slot, a lower gas-collecting chamber and a lower pressure-releasing chamber, wherein the gas-collecting slot is concavely formed on a bottom surface spatially corresponding to the gas-flow slot, wherein the lower gas-collecting chamber and the lower pressure-releasing chamber are formed on a top surface of the gas-collector seat, wherein a gas-collecting perforation is formed and disposed between the gas-collecting slot and the lower gas-collecting chamber to allow the gas-collecting slot and the lower gas-collecting chamber to communicate with each other, wherein the lower gas-collecting chamber and the lower pressure-releasing chamber are separated apart on the top surface of the gas-collecting seat, and a communication channel is disposed between the lower gas-collecting chamber and the lower pressure-releasing chamber to allow the lower gas-collecting chamber and the lower pressure-releasing chamber to communicate with each other, wherein a first protrusion is formed in the lower pressure-releasing chamber and a pressure-releasing perforation is disposed at a center of the first protrusion, wherein the pressure-releasing perforation is in fluid communication with the lower pressure-releasing chamber and the exhausting aperture of the cover plate, wherein the elastic air-bag is in fluid communication with the gas-collecting slot and the gas-collecting perforation, and the chamber plate is carried and disposed on the gas-collecting seat, wherein the chamber plate comprises an upper gas-collecting chamber and an upper pressure-releasing chamber formed on a top surface spatially corresponding to the gas-collecting seat, wherein the upper gas-collecting chamber and the lower gas-collecting chamber are matched and sealed with each other, and the upper pressure-releasing chamber and the lower pressure-releasing chamber are matched and sealed with each other, wherein a second protrusion is formed in the upper gas-collecting chamber, and a communication chamber is concavely formed on a bottom surface of the chamber plate opposite to the upper gas-collecting chamber and the upper pressure-releasing chamber, wherein the gas-collecting actuator is carried and disposed on the chamber plate to seal and cover the communication chamber, and at least one communication aperture communicates with the communication chamber and is in fluid communication with the upper gas-collecting chamber and the upper pressure-releasing chamber, wherein the valve membrane is disposed between the gas-collector seat and the chamber plate and abutted against the first protrusion to seal the pressure-releasing perforation, wherein the valve membrane has a valve aperture disposed at a position abutted against the second protrusion, and the valve aperture is sealed by abutting against the second protrusion.

7. The wearable health monitoring device according to claim 6, wherein the gas-collecting actuator is controlled and driven to transport the gas, wherein the gas is inhaled and collected in the communication chamber, and then transported from the communication chamber to the upper gas-collecting chamber and the upper pressure-releasing chamber through the communication aperture, whereby the valve membrane is pushed to move apart from the second protrusion, the valve membrane is pushed to abut against the first protrusion and to seal the pressure-releasing perforation, and the gas in the upper pressure-releasing chamber is transported into the upper gas-collecting chamber through the communication channel and further transport into the lower gas-collecting chamber through the valve aperture of the valve membrane, wherein the gas is converged to the gas-collecting slot to inflate the elastic air-bag, and the elastic air-bag is inflated and elastically protrudes out of the cover plate, so as to attach to the skin tissue of the wearing user.

8. The wearable health monitoring device according to claim 7, wherein the elastic air-bag has a pressing plate disposed on an inflatable end thereof configured to abut against and attach the skin tissue of the wearing user.

9. The wearable health monitoring device according to claim 7, wherein when the gas-collecting actuator stops transporting gas, gas pressure of the elastic air-bag is greater than that of the communication chamber, whereby the gas converged in the elastic air-bag pushes the valve membrane to move and abut against the second protrusion, the valve aperture is sealed, and the gas pushes the valve membrane to move apart from the first protrusion to open the pressure-releasing perforation, wherein the gas converged in the elastic air-bag is transported to the pressure-releasing perforation and discharged out of the air-pressure-based blood pressure meter, so that a pressure-releasing operation of the elastic air-bag is performed.

10. The wearable health monitoring device according to claim 1, wherein the gas-collecting actuator is a micro pump, and the micro pump comprises:
   a gas inlet plate having at least one inlet aperture, at least one convergence channel and a convergence chamber, wherein the at least one inlet aperture allows the gas to flow in, and the convergence channel is disposed correspondingly to the inlet aperture and guides the gas from the inlet aperture toward the convergence chamber;
   a resonance plate having a central aperture, a movable part and a fixing part, wherein the central aperture is disposed at a center of the resonance plate and aligned with the convergence chamber of the gas inlet plate, the movable part surrounds the central aperture and spatially corresponds to the convergence chamber, and the fixing part is located at a peripheral portion of the resonance plate and is attached on the gas inlet plate;
   a piezoelectric actuator facing and assembled with the resonance plate;
   a first insulation plate,
   a conducting plate; and
   a second insulation plate,
   wherein the gas inlet plate, the resonance plate, the piezoelectric actuator, the first insulation plate, the conducting plate and the second insulation plate are stacked sequentially, wherein a chamber space is formed between the resonance plate and the piezoelectric actuator, wherein when the piezoelectric actuator is driven, the gas is introduced into the at least one inlet aperture of the gas inlet plate, converged to the convergence chamber along the at least one convergence channel, and flows into the central aperture of the resonance plate, whereby the gas is further transported through a resonance between the piezoelectric actuator and the movable part of the resonance plate.

11. The wearable health monitoring device according to claim 10, wherein the piezoelectric actuator comprises:
   a suspension plate being a square suspension plate and permitted to undergo a bending vibration;
   an outer frame arranged around the suspension plate;
   at least one bracket connected between the suspension plate and the outer frame for elastically supporting the suspension plate; and
   a piezoelectric element, wherein a length of a side of the piezoelectric element is smaller than or equal to a length of a side of the suspension plate, and the piezoelectric element is attached on a surface of the suspension plate to drive the suspension plate to undergo the bending vibration in response to an applied voltage,
   wherein the suspension plate has a bulge, a first surface and a second surface opposite to the first surface, wherein the bulge is disposed on the second surface opposite to the first surface attached to the piezoelectric element, wherein the bulge is formed by an etching process, and the bulge is a convex structure integrally formed on the second surface opposite to the first surface of the suspension plate attached to the piezoelectric element.

12. The wearable health monitoring device according to claim 10, wherein the piezoelectric actuator comprises:
a suspension plate being a square suspension plate and permitted to undergo a bending vibration;
an outer frame arranged around the suspension plate;
at least one bracket connected between the suspension plate and the outer frame for elastically supporting the suspension plate, wherein a non-coplanar structure is formed on a surface of the suspension plates and a surface of the outer frame, and a cavity space is maintained between the surface of the suspension plate and the resonance plate; and
a piezoelectric element, wherein a length of a side of the piezoelectric element is smaller than or equal to a length of a side of the suspension plate, and the piezoelectric element is attached on the surface of the suspension plate to drive the suspension plate to undergo the bending vibration in response to an applied voltage.

13. The wearable health monitoring device according to claim 10, wherein the micro pump is microelectromechanical-system micro pump.

14. The wearable health monitoring device according to claim 2, further comprises a control module, and the control module includes a microprocessor, a communicator and a global positioning system component, wherein the detection signals of the photoelectric sensor, the pressure sensor and the impedance sensor are converted into health data information to output by the microprocessor, wherein the communicator comprises an Internet of Things (IoT) communication component and a data communication component, the Internet of Things communication component receives the health data information from the biometric monitoring module and transmits the health data information to an external link device to store and record for further analysis and statistics, so as to better understand a health condition of the wearing user better, wherein the Internet of Things communication component is a narrowband Internet of Things device transmitting a transmission signal by a narrowband radio communication technology, wherein the external link device comprises a network repeater and a cloud data processing device, wherein the Internet of Things communication component transmits the health data information to the cloud data processing device to store and record through the network repeater for further analysis and statistics, so as to better understand the health condition of the wearing user.

15. The wearable health monitoring device according to claim 14, wherein the data communication component receives the health data information from the biometric monitoring module and transmits the health data information to the external link device to store and record for further analysis and statistics, so as to better understand the health condition of the wearing user, wherein data communication component transmits the health data information through a wireless communication transmission interface.

16. The wearable health monitoring device according to claim 14, wherein the external link device comprises a mobile communication link device, the network repeater and the cloud data processing device, wherein the mobile communication link device is at least one selected form the group consisting of a mobile phone device, a notebook computer and a tablet computer, wherein the mobile communication link device receives the health data information and further transmits the health data information to the cloud data processing device to store and record through the network repeater for further analysis and statistics, so as to know the health condition of the wearing user.

17. A wearable health monitoring device comprising:
a monitoring main-body comprising an embedding seat, a monitoring-zone slot and a cover plate, wherein the embedding seat has an embedding slot portion concavely formed and a bottom of the embedding slot portion is in fluid communication with a gas-flow slot and an exhausting channel, wherein an air-bag channel is disposed on a side of the embedding seat and in fluid communication with the gas-flow slot, wherein the monitoring-zone slot is adjacent to a side of the embedding seat, wherein the cover plate covers the bottom of the embedding slot portion and has an exhausting aperture passing therethrough and spatially corresponding to a position of the exhausting channel, and a transparent mask spatially corresponding to a position of the monitoring-zone slot;
a wearable component connected to an outside of the monitoring main-body, wherein an elastic air-bag is disposed around an inner annulus of the wearable component, and comprises an inlet end embedded and fixed in the air-bag channel of the embedding seat; and
a biometric monitoring module disposed within the monitoring main-body and comprising a photoelectric sensor, a pressure sensor and an air-pressure-based blood pressure meter, wherein the photoelectric sensor and the pressure sensor are disposed and positioned in the monitoring-zone slot to perform monitoring, and the air-pressure-based blood pressure meter is embedded and positioned in the embedding slot portion of the embedding seat, wherein the air-pressure-based blood pressure meter comprises a gas-collecting actuator, a gas-collector seat, a chamber plate and a valve membrane, wherein the gas-collector seat comprises a gas-collecting slot, and the gas-collecting slot is in fluid communication with the gas-flow slot of the embedding seat and the air-bag channel, wherein the gas-collecting actuator transports a gas from the gas-collecting slot to the elastic air-bag through the air-flow slot and the air-bag channel, and the elastic air-bag is inflated and elastically protrudes out of the inner annulus of the wearable component, whereby the elastic air-bag is capable of being attached to a skin tissue of a wearing user, and the pressure sensor is capable of measuring vasoconstriction pulsation under the skin tissue and generates a detection signal accordingly, wherein the detection signal is converted into health data information and is outputted, wherein the health data information is provided to the photoelectric sensor for calibrating a calculation of the detection signal thereof to output precise health data information.

18. The wearable health monitoring device according to claim 17, wherein the gas-collector seat is disposed on the embedding slot portion, the gas-collecting slot is concavely formed on a bottom surface spatially corresponding to the gas-flow slot, wherein a lower gas-collecting chamber and a lower pressure-releasing chamber formed on a top surface of the gas-collector seat, wherein a gas-collecting perforation is disposed between the gas-collecting slot and the lower gas-collecting chamber to allow the gas-collecting slot and the lower gas-collecting chamber to communicate with each other, wherein the lower gas-collecting chamber and the lower pressure-releasing chamber are separated apart on the top surface of the gas-collecting seat, and a communication channel is disposed between the lower gas-collecting chamber and the lower pressure-releasing chamber to allow the lower gas-collecting chamber and the lower pressure-releasing chamber to communicate with each other, wherein a first protrusion is formed in the lower pressure-releasing chamber and a pressure-releasing perforation is disposed at a center of the first protrusion, wherein the pressure-releasing perforation is in fluid communication with the lower pressure-releasing chamber and the exhausting aperture of the cover plate, wherein the chamber plate is carried and disposed on the gas-collecting seat, and the chamber plate comprises an upper gas-collecting chamber and an upper pressure-releasing chamber formed on a top surface spatially corresponding to the gas-collecting seat, wherein the upper gas-collecting chamber and the lower gas-collecting chamber are matched and sealed with each other, and the upper pressure-releasing chamber and the lower pressure-releasing chamber are matched and sealed with each other, wherein a second protrusion is formed in the upper gas-collecting chamber, and a communication chamber is concavely formed on a bottom surface of the chamber plate opposite to the upper gas-collecting chamber and the upper pressure-releasing chamber, wherein the gas-collecting actuator is carried and disposed on the chamber plate to seal and cover the communication chamber, and at least one communication aperture communicates with the communication chamber and in fluid communication with the upper gas-collecting chamber and the upper pressure-releasing chamber, wherein the valve membrane is disposed between the gas-collector seat and the chamber plate and abutted against the first protrusion to seal the pressure-releasing perforation, wherein the valve membrane has a valve aperture disposed at a position abutted against the second protrusion, and the valve aperture is sealed by abutting against the second protrusion.

19. The wearable health monitoring device according to claim 18, wherein the gas-collecting actuator is controlled and driven to transport the gas, wherein the gas is inhaled and collected in the communication chamber, and then transported from the communication chamber to the upper gas-collecting chamber and the upper pressure-releasing chamber through the communication aperture, whereby the valve membrane is pushed to move apart from the second protrusion, the valve membrane is pushed to abut against the first protrusion and to seal the pressure-releasing perforation, and the gas in the upper pressure-releasing chamber is transported into the upper gas-collecting chamber through the communication channel and further transport into the lower gas-collecting chamber through the valve aperture of the valve membrane, wherein the gas is converged to the gas-collecting slot and further transported through the gas-flow slot and the air-bag channel to inflate the elastic air-bag, and the elastic air-bag is inflated and elastically protrudes out of the inner annulus of the wearable component, so as to attach to the skin tissue of the wearing user.

20. The wearable health monitoring device according to claim 18, wherein when the gas-collecting actuator stops transporting gas, gas pressure of the elastic air-bag is greater than that of the communication chamber, whereby the gas converged in the elastic air-bag pushes the valve membrane to move and abut against the second protrusion, the valve aperture is sealed, and the gas pushes the valve membrane to move apart from the first protrusion to open the pressure-releasing perforation, wherein the gas converged in the elastic air-bag is transported to the pressure-releasing perforation and discharged out of the air-pressure-based blood pressure meter, so that a pressure-releasing operation of the elastic air-bag is performed.

* * * * *